United States Patent

Bartroli et al.

Patent Number: 5,807,854
Date of Patent: Sep. 15, 1998

[54] PYRIMIDONE DERIVATIVES WITH ANTIFUNGAL ACTIVITY

[75] Inventors: Javier Bartroli; Enric Turmo; Manuel Anguita, all of Barcelona, Spain

[73] Assignee: J. Uriah & Cia. S.A., Barcelona, Spain

[21] Appl. No.: 809,967

[22] PCT Filed: Aug. 2, 1996

[86] PCT No.: PCT/EP96/03420

§ 371 Date: Mar. 21, 1997

§ 102(e) Date: Mar. 21, 1997

[87] PCT Pub. No.: WO97/05130

PCT Pub. Date: Feb. 3, 1997

[30] Foreign Application Priority Data

Aug. 2, 1995 [ES] Spain ..................... 9501564
Mar. 15, 1996 [ES] Spain ..................... 9600646

[51] Int. Cl.$^6$ ............ C07D 403/02; C07D 403/14; A61K 31/505; A61K 31/495

[52] U.S. Cl. .......... 514/248; 514/249; 514/250; 514/258; 514/259; 514/261; 514/262; 514/263; 514/264; 514/265; 514/267; 544/284; 544/279; 544/256; 544/280; 544/278; 544/264; 544/265; 544/266; 544/267; 544/268; 544/269; 544/270; 544/271; 544/272; 544/255; 544/262; 544/249; 544/236; 544/250; 544/251; 544/254; 544/257; 544/258; 544/259; 544/260; 544/261

[58] Field of Search ............ 544/284, 279, 544/256, 280, 278, 264–272, 255, 262, 249, 234, 250, 251, 257–261, 254; 514/259, 258, 261–265, 267, 248, 249, 250

[56] References Cited

FOREIGN PATENT DOCUMENTS 0 357 241 3/1990 European Pat. Off. .
0 293 500 11/1993 European Pat. Off. .
0 567 982 11/1993 European Pat. Off. .

*Primary Examiner*—Matthew V. Grumbling
*Attorney, Agent, or Firm*—Burns, Doane, Swecker & Mathis, L.L.P.

[57] ABSTRACT

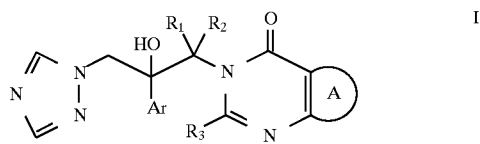

Compounds of general formula I and their salts and solvates are antifungal agents and as such are useful in the treatment of various fungal infections. Pharmaceutical compositions including these compounds and processes for their preparation are also provided.

19 Claims, No Drawings

PYRIMIDONE DERIVATIVES WITH ANTIFUNGAL ACTIVITY

FIELD OF THE INVENTION

The present invention relates to a new series of pyrimidone derivatives of general formula I having potent antifungal activity. The invention also relates to a process for their preparation, to pharmaceutical compositions containing them and to their use for the treatment of fungal diseases.

1. Description of the Prior Art

The compounds of the present invention are antifungal agents belonging to the azole class, whose mechanism of action is based on the inhibition of the biosynthesis of ergosterol, the main sterol present in fungi membranes. Other antifungal agents having this mechanism of action have been reported in the literature and some of them are already being used in therapy. Some of them are administered topically in the treatment of fungal infections in skin, vagina and nails. More recently discovered compounds are used orally in the treatment of systemic and organ mycoses, such as systemic candidiasis, aspergillosis, criptococcal meningitis, coccidioidomycosis, paracoccidioidomycosis, histoplasmosis, chromoblastomycosis, sporotrichosis, and blastomycosis.

However, given the worrying rise in fungal infections, specially among immunocompromised patients (such as AIDS patients or cancer patients undergoing chemotherapy) and the emergence of pathogens resistant to some of the commonly used antifungal agents, the present medical situation is by no means satisfactory and new orally active products which are more potent, have a broader spectrum of antifungal activity and which are effective against certain mycoses (such as aspergillosis) for which no effective treatment is currently available are urgently needed.

2. Description of the Invention

The present invention relates to new pyrimidone derivatives of general formula I

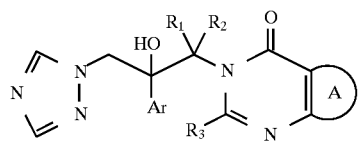

as racemates, diastereomer mixtures or as pure enantiomers, wherein:

Ar represents phenyl or phenyl substituted with one or more halogen and/or trifluoromethyl groups;

$R_1$ is $C_1$–$C_4$ alkyl;

$R_2$ is hydrogen or $C_1$–$C_4$ alkyl; or $R_1$ together with $R_2$ form a $C_2$–$C_4$ polymethylene chain;

$R_3$ represents hydrogen, $C_1$–$C_4$ alkyl, $C_1$–$C_4$ haloalkyl, or cyclopropyl;

A represents a benzene ring or a 5- or 6-membered heterocyclic ring wherein one or more of the ring atoms are selected from the group consisting of N, O and S, which rings can be optionally fused to a benzene ring or to a 5- or 6-membered heterocyclic ring containing one or more heteroatoms selected from N, O and S, and wherein A can be unsubstituted or have 1, 2, 3 or 4 substituents W in any of the rings;

a group W represents $C_1$–$C_4$ alkyl, $C_3$–$C_6$ cycloalkyl, $C_1$–$C_4$ haloalkyl, $C_1$–$C_4$ alkoxy, $C_1$–$C_4$ haloalkoxy, halogen, nitro, cyano, hydroxy, benzyloxy, hydroxymethyl, a group —$NR_4R_5$, a group —$CONR_4R_5$, a group —$CH_2$—OCO—$R_4$, a group —CO—$R_4$, a group —COO—$R_4$, a group —$SO_zR_6$, a group —C(=$NR_4$)$NHR_7$, a group —C(=$NR_7$)$OR_4$, and additionally one of the groups W can also represent 1-pyrrolyl, 1-imidazolyl, 1H-1,2,4-triazol-1-yl, 5-tetrazolyl (optionally substituted with $C_1$–$C_4$ alkyl), 1-pyrrolidinyl, 4-morpholinyl, 4-morpholinyl-N-oxide, a group —X—$R_8$, or a group of formula (i)–(iv):

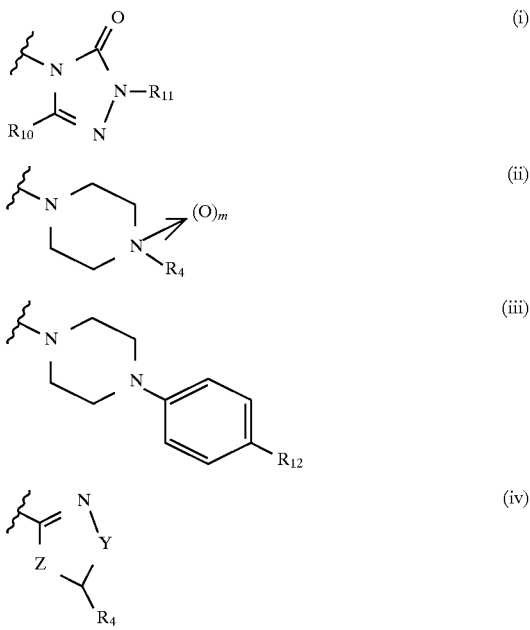

wherein

R represents hydrogen, $C_1$–$C_4$ alkyl, $C_3$–$C_6$ cycloalkyl or aryl $C_{1-4}$ alkyl, wherein aryl represents phenyl or phenyl substituted with one or more $C_1$–$C_4$ alkyl, halogen, $C_1$–$C_4$ haloalkyl, $C_1$–$C_4$ alkoxy or $C_1$–$C_4$ haloalkoxy groups;

$R_5$ represents hydrogen, $C_1$–$C_4$ alkyl, $C_3$–$C_6$ cycloalkyl, a group —$COR_4$ or a group —$COCF_3$;

$R_6$ represents $C_1$–$C_4$ alkyl;

z represents 0, 1 or 2;

$R_7$ represents hydrogen, —$CONH_2$, —COMe, —CN, —$SO_2NHR_4$, —$SO_2R_4$, —$OR_4$, —$OCCOR_4$ or —($C_{1-4}$ alkyl)—$NH_2$;

X represents a single bond, —O—, —$SO_z$—, —$NR_4$—, or —C(=O)—;

$R_8$ represents a phenyl group optionally substituted with one or more groups $R_9$;

$R_9$ represents $C_1$–$C_4$ alkyl, $C_3$–$C_6$ cycloalkyl, $C_1$–$C_4$ haloalkyl, $C_1$–$C_4$ alkoxy, $C_1$–$C_4$ haloalkoxy, halogen, nitro, cyano, a group —$NR_4R_5$, a group —$CONR_4R_5$, a group —$CH_2$—OCO—$R_4$, a group —CO—$R_4$, a group —COO—$R_4$, a group —$SO_zR_6$, a group —C(=$NR_4$)$NHR_7$, a group —C(=$NR_7$)$OR_4$, a group of formula (iv) or $R_9$ represents a phenyl group (optionally substituted with a group $C_1$–$C_4$ alkyl, $C_1$–$C_4$ haloalkyl, $C_1$–$C_4$ alkoxy, $C_1$–$C_4$ haloalkoxy, halogen, nitro or cyano);

$R_{10}$ represents hydrogen or methyl;

$R_{11}$ represents hydrogen, isopropyl, cyclopentyl, cyclopropyl, 2-butyl, 3-pentyl, 3-hydroxy-2-butyl, or 2-hydroxy-3-pentyl;

m represents 0 or 1;

$R_{12}$ represents halogen, $C_1$–$C_4$ haloalkyl, $C_1$–$C_4$ haloalkoxy, nitro, amino, cyano, or a group of formula (i);

Y represents —$CH_2$— or —C(=O)—; and

Z represents NH or O;

and the salts and solvates thereof.

The invention also provides a pharmaceutical composition which comprises an effective amount of a compound of formula I or a pharmaceutically acceptable salt or solvate thereof in admixture with one or more pharmaceutically acceptable excipients.

The invention further provides the use of a compound of formula I or a pharmaceutically acceptable salt or solvate thereof for the manufacture of a medicament for the treatment or prophylaxis of fungal infections in animals, including human beings.

The invention further provides the use of a compound of formula I or a pharmaceutically acceptable salt or solvate thereof for the treatment or prophylaxis of fungal infections in animals, including human beings.

The invention also provides a method of treating or preventing fungal infections in animals, including human beings, which method comprises administering to a patient in need thereof an effective amount of a compound of formula I or a pharmaceutically acceptable salt or solvate thereof.

In addition to being useful for the treatment of fungal infections in animals, the compounds of the present invention possess antifungal properties which can be useful for combatting or preventing plant fungal infections. The invention thus provides the use of a compound of formula I or a salt or solvate thereof for the treatment or prophylaxis of fungal infections in plants.

The invention still further provides an agrochemical composition which comprises an effective amount of a compound of formula I or a salt or solvate thereof in admixture with one or more agrochemically acceptable excipients.

The invention also provides a process for preparing a compound of formula I, which comprises:

(a) reacting a compound of formula II

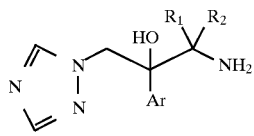

wherein $R_1$, $R_2$ and Ar are as defined above, first with an acid of formula III

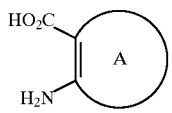

wherein A is as defined above, in the presence of a condensing agent, and then with an acid $R_3$COOH (wherein $R_3$ is as defined above) or a reactive derivative thereof such as the alkyl imidate, amidine, acid chloride, anhydride or orthoester; or (b) reacting a compound of formula II with a compound of formula IV

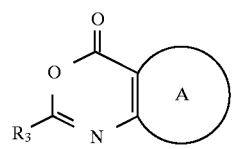

wherein $R_3$ and A are as defined above; or (c) converting in one or a plurality of steps a compound of formula I into another compound of formula I; and (d) if desired, after steps (a), (b) or (c), reacting a compound of formula I with an acid to give the corresponding acid addition salt.

In the above definitions, the term $C_1$–$C_4$ alkyl, as a group or part of a group, means a linear or branched alkyl chain containing from 1 to 4 carbon atoms. Therefore, it includes methyl, ethyl, propyl, isopropyl, butyl, isobutyl, sec-butyl, and tert-butyl.

A $C_2$–$C_4$ polymethylene chain means ethylene, propylene or butylene.

A $C_{1-4}$ haloalkyl group means a group resulting from the substitution of one or more hydrogen atoms of a $C_{1-4}$ alkyl group by one or more halogen atoms (i.e. fluorine, chlorine, bromine or iodine), which can be the same or different. Examples include trifluoromethyl, trichloromethyl, fluoromethyl, chloromethyl, bromomethyl, iodomethyl, difluoromethyl, dichloromethyl, 2-chloroethyl, 2,2-dichloroethyl, 2,2,2-trichloroethyl, pentachloroethyl, 2-fluoroethyl, 2,2-difluoroethyl, 2,2,2-trifluoroethyl, pentafluoroethyl, 3-chloropropyl, 3,3-dichloropropyl, 3,3,3-trichloropropyl, 2,2,3,3,3-pentachloropropyl, 3-fluoropropyl, 3,3-difluoropropyl, 3,3,3-trifluoropropyl, 2,2,3,3-tetrafluoropropyl, 2,2,3,3,3-pentafluoropropyl, heptafluoropropyl, 4-chlorobutyl, 4-fluorobutyl, 4-iodobutyl and 4-bromobutyl.

A $C_3$–$C_6$ cycloalkyl group represents cyclopropyl, cyclobutyl, cyclopentyl or cyclohexyl.

A $C_{1-4}$ alkoxy group means a group derived from the union of a $C_{1-4}$ alkyl group to an oxygen atom of an ether functional group. Examples include methoxy, ethoxy, propoxy, isopropoxy, butoxy, isobutoxy, sec-butoxy and tert-butoxy.

A $C_{1-4}$ haloalkoxy group means a group resulting from the substitution of one or more hydrogen atoms of a $C_{1-4}$ alkoxy group by one or more halogen atoms, which can be the same or different. Examples include trifluoromethoxy, fluoromethoxy, 2-chloroethoxy, 2-fluoroethoxy, 2-iodoethoxy, 2,2-difluoroethoxy, 2,2,2-trifluoroethoxy, pentafluoroethoxy, 3-fluoropropoxy, 3-chloropropoxy, 2,2,3,3-tetrafluoropropoxy, 2,2,3,3,3-pentafluoropropoxy, heptafluoropropoxy, 4fluorobutoxy, and 4-chlorobutoxy.

In the compounds of the present invention Ar represents a phenyl group or a phenyl group substituted with one or more halogen and/or trifluoromethyl groups. The halogen atoms may be fluorine, chlorine, bromine or iodine atoms, of which fluorine and chlorine atoms are preferred. There may be one or more such substituents on the phenyl group, and where there are more than one, these may be the same or different. When the phenyl group is substituted, the substituents can be on any available position of the phenyl ring, but they are preferably on the 2- and/or 4-positions. Examples of substituted phenyl groups include 4-(trifluoromethyl)phenyl, 2-fluorophenyl, 4-fluorophenyl, 2-chloro-4-fluorophenyl, 4-chloro-2-fluorophenyl, 4-bromophenyl, 2-fluoro-4-iodophenyl, 2,4-dichlorophenyl, 2,4-difluorophenyl, 4-chlorophenyl and 2-fluoro-4-(trifluoromethyl)phenyl, of which 2-fluorophenyl, 4-fluorophenyl, 2-chloro-4-fluorophenyl, 2,4-dichlorophenyl, 2,4-difluorophenyl, 4-(trifluoromethyl) phenyl and 4-chlorophenyl are preferred, and 2-fluorophenyl, 2,4-dichlorophenyl, 2,4-difluorophenyl, 4-(trifluoromethyl)phenyl and 4-chlorophenyl are more preferred.

In the compounds of the present invention $R_1$ represents a $C_1$–$C_4$ alkyl group, or together with $R_2$ forms a $C_2$–$C_4$ polymethylene chain, but preferably $R_1$ is $C_1$–$C_4$ alkyl, and more preferably $R_1$ is methyl.

In the compounds where $R_2$ is hydrogen or $C_1$–$C_4$ alkyl, or together with $R_1$ forms a $C_2$–$C_4$ polymethylene chain, those wherein $R_2$ is hydrogen or methyl are preferred, and those wherein $R_2$ is hydrogen are more preferred.

As for substituent $R_3$, those compounds wherein $R_3$ represents hydrogen, methyl, trifluoromethyl or cyclopropyl are preferred, and those wherein $R_3$ is hydrogen are more preferred.

In the compounds of the present invention, A completes a benzene ring or a 5- or 6-membered heterocyclic ring, which rings can be both optionally fused to a benzene ring or to a 5- or 6-membered heterocyclic ring. As used herein, a 5- or 6-membered heterocyclic ring refers to such rings having from 5 to 6 atoms in the ring wherein one or more, preferably 1 to 3, of said ring atoms are heteroatoms selected from the group consisting of N, O and S. Thus, heterocycles containing a nitrogen, oxygen or sulphur atom alone, or containing two nitrogen atoms, a nitrogen and an oxygen atom, a nitrogen and a sulphur atom, two nitrogen atoms and an oxygen atom, two nitrogen atoms and a sulphur atom, or three nitrogen atoms are possible. Moreover, system A can be unsubstituted or have 1, 2, 3 or 4 substituents W as defined above, which can be on any available position of any of the rings. When there is more than one substituent W on ring A, they can be the same or different provided that, as mentioned above in connection with the definition of W in formula I, for certain meanings of W there cannot be more than one such group on ring A.

In the compounds wherein A represents a benzene ring, this can be unsubstituted or, as stated above, it can be substituted with 1, 2, 3 or 4 groups W. Following the ring numbering shown in the following formula

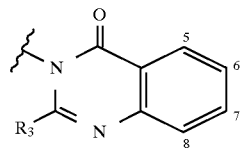

are preferred examples of substituents of the benzene ring the groups 5-chloro, 6-chloro, 7-chloro, 8-chloro, 5-fluoro, 6-fluoro, 7-fluoro, 8-fluoro, 6-bromo, 7-bromo, 5-trifluoromethyl, 6-trifluoromethyl, 7-trifluoromethyl, 8-trifluoromethyl, 6,8-dichloro, 6,8-difluoro, 5,7-dichloro, 5,7-difluoro, 6,7-dichloro, 6,7-difluoro, 6-chloro-7-fluoro, 7,8-dichloro, 7,8-difluoro, 7-bromo-6-fluoro, 7-bromo-6-chloro, 7-methyl, 7-isopropyl, 7-tert-butyl, 7-(N,N-dimethyl)amino, 7-(1-methyl-4-piperazinyl), 7-(1-pyrrolyl), 7-(1-imidazolyl), 7-(1H-1,2,4-triazolyl), 7-(4-pyrrolidinyl), 7-(4-morpholinyl), 7-(4-morpholinyl-N-oxide), 7-nitro, 7-methoxy, 7-trifluoromethoxy, 7-(2-fluoroethoxy), 7-(2,2-difluoroethoxy), 7-(2,2,2-trifluoroethoxy), 7-(2,2,3,3-tetrafluoropropoxy), 7-(2,2,3,3,3-pentafluoropropoxy), 7-methylthio, 7-cyano, 7-[amino(imino)methyl], 7-[(aminosulfonylamino)(imino)methyl], 6-fluoro-7-methyl, 6-fluoro-7-isopropyl, 6-fluoro-7-tert-butyl, 7-(N,N-dimethyl)amino-6-fluoro, 6-fluoro-7-(1-methyl-4-piperazinyl), 6-fluoro-7-(1-pyrrolyl), 6-fluoro-7-(1-imidazolyl), 6-fluoro-7-(1H-1,2,4-triazolyl), 6-fluoro-7-(1-pyrrolidinyl), 6-fluoro-7-(4-morpholinyl), 6-fluoro-7-(4-morpholinyl-N-oxide), 6-fluoro-7-nitro, 6-fluoro-7-methoxy, 6-fluoro-7-trifluoromethoxy, 6-fluoro-7-(2-fluoroethoxy), 7-(2,2-difluoroethoxy)-6-fluoro, 6-fluoro-7-(2,2,2-trifluoroethoxy), 6-fluoro-7-(2,2,3,3-tetrafluoropropoxy), 6-fluoro-7-(2,2,3,3,3-pentafluoropropoxy), 6-fluoro-7-methylthio, 7-cyano-6-fluoro, 7-[amino(imino)methyl]-6-fluoro, 7-[(aminosulfonylamino) (imino)methyl]-6-fluoro, 6-fluoro-7-trifluoromethyl, 7-chloro-6-fluoro, 5,6,7,8-tetrafluoro, 5-fluoro-7-trifluoromethyl, 5-chloro-7-trifluoromethyl, 6-methoxy, 6,7-dimethoxy, 7-(4-chlorophenoxy), 7-(4-chlorophenoxy)-6-fluoro, 7-[4-(4-chlorophenyl)-1-piperazinyl], 6-fluoro-7-[4(4-chlorophenyl)-1-piperazinyl], 7-[4-[4[2,4-dihydro-2-(3-pentyl)-3H-1,2,4-triazol-3-one-4-yl]phenyl]-1-piperazinyl], 6-fluoro-7-[4-[4-[2,4-dihydro-2-(3-pentyl)-3H-1,2,4-triazol-3-one-4-yl]phenyl]-1-piperazinyl], 7-[4-[4-[2,4-dihydro-2-(2-hydroxy-3-pentyl)-3H-1,2,4-triazol-3-one-4-yl]phenyl]-1-piperazinyl] or 6-fluoro-7-[4-[4-[2,4-dihydro-2-(2-hydroxy-3-pentyl)-3H-1,2,4triazol-3-one-4yl]phenyl]-1-piperazinyl].

When A represents a benzene ring fused to a second ring, which can be a further benzene ring or a 5- or 6-membered heterocycle, examples of A include naphthalene, benzofuran, benzothiophene, indole, quinoline, isoquinoline, quinoxaline, quinazoline, cinnoline, benzimidazole, benzothiazole and benzofurazan.

In the compounds wherein A represents a 5- or 6-membered heterocyclic ring wherein one or more of the ring atoms are nitrogen and/or oxygen and/or sulphur, this can be unsubstituted or have 1, 2, 3 or 4 groups W (which can be placed on any available position of ring A) and can be fused to the pyrimidone nucleus by any of its sides provided that the fusion side does not contain one or more heteroatoms. Furthermore, ring A can be optionally fused to a benzene ring or to a further 5- or 6-membered heterocyclic ring, in which case the substituents W can be on any available position of the fused cyclic system. Examples of 6-membered heterocycles containing one nitrogen atom and fused to the pyrimidone moiety by any of the sides b, c, d or e are pyridine and piperidine. Examples of 6-membered heterocycles containing two nitrogen atoms are pyrimidine fused by any of its sides d and e, pyrazine and piperazine fused by any of their sides b and e, and pyridazine fused by any of its sides c, d or e. Examples of 5-membered heterocycles containing one heteroatom and fused by sides b or d are thiophene, pyrrole and furan. Examples of 5-membered heterocycles containing two heteroatoms and fused by side d are imidazole, thiazole and oxazole. Examples of 5-membered heterocycles containing two heteroatoms and fused by sides d or c are pyrazole, isoxazole and isothiazole. Examples of A systems formed by a heterocyclic ring fused to a second ring include among others benzofuran, benzothiophene, indole, quinoline, thienopyridine, thienopyrimidine, imidazopyridine, imidazopyrimidine, thiazolopyridine, thiazolopyrimidine, and naphthyridine.

Although A can have all the above mentioned meanings, those wherein A represents a benzene ring, which can be optionally fused to a benzene ring or to a 5- or 6-membered heterocyclic ring containing one or more heteroatoms selected from N, O and S, or A represents a 5- or 6-membered heterocyclic ring, wherein one or more of said ring atoms are selected from the group consisting of N, O and S, which heterocyclic ring can be optionally fused to a benzene ring, are preferred; those wherein A represents a benzene ring or a 5- or 6-membered heterocyclic ring containing one or more heteroatoms selected from N, O and S are more preferred; those wherein A represents a benzene ring or a 5-membered heterocyclic ring containing one heteroatom selected from N, O and S or two heteroatoms selected from the pairs N/N, N/O and N/S are still more preferred; and those wherein A represents a benzene, thiophene or thiazole ring are particularly preferred. All these A groups can be unsubstituted or substituted with 1, 2, 3 or 4 groups W.

Preferred compounds of the present invention include those in which, independently or in any compatible combination:

$R_1$ represents $C_{1-4}$ alkyl;
$R_2$ represents hydrogen;
$R_3$ represents hydrogen, methyl, trifluoromethyl or cyclopropyl;
Ar represents 2-fluorophenyl, 4-fluorophenyl, 2-chloro-4-fluorophenyl, 2,4-dichlorophenyl, 2,4-difluorophenyl, 4-(trifluoromethyl)phenyl or 4-chlorophenyl;
A represents a benzene ring, which can be optionally fused to a benzene ring or to a 5- or 6-membered heterocyclic ring containing one or more heteroatoms selected from N, O and S, or A represents a 5- or 6-membered heterocyclic ring, wherein one or more of said ring atoms are selected from the group consisting of N, O and S, which heterocyclic ring can be optionally fused to a benzene ring, wherein A can be unsubstituted or have 1, 2, 3 or 4 groups W in any of the rings;
the stereochemistry of the compounds is (1R,2R).

Particularly preferred compounds of the present invention include those in which, independently or in any compatible combination:

$R_1$ represents methyl;
$R_2$ represents hydrogen;
$R_3$ represents hydrogen;
Ar represents 2-fluorophenyl, 2,4-dichlorophenyl, 2,4-difluorophenyl, 4-(trifluoromethyl)phenyl or 4-chlorophenyl;
A represents a benzene ring or a 5- or 6-membered heterocyclic ring containing one or more heteroatoms selected from N, O and S, wherein A can be unsubstituted or have 1, 2, 3 or 4 groups W;
the stereochemistry of the compounds is (1R,2R).

Accordingly, a preferred class of compounds of formula I is that wherein:

$R_1$ represents $C_{1-4}$ alkyl;
$R_2$ represents hydrogen;
$R_3$ represents hydrogen, methyl, trifluoromethyl or cyclopropyl;
Ar represents 2-fluorophenyl, 4-fluorophenyl, 2-chloro-4-fluorophenyl, 2,4-dichlorophenyl, 2,4-difluorophenyl, 4-(trifluoromethyl)phenyl or 4-chlorophenyl;
A represents a benzene ring, which can be optionally fused to a benzene ring or to a 5- or 6-membered heterocyclic ring containing one or more heteroatoms selected from N, O and S, or A represents a 5- or 6-membered heterocyclic ring, wherein one or more of said ring atoms are selected from the group consisting of N, O and S, which heterocyclic ring can be optionally fused to a benzene ring, wherein A can be unsubstituted or have 1, 2, 3 or 4 groups W in any of the rings; and
the stereochemistry of the compounds is (1R,2R).

A more preferred class of compounds of formula I is that wherein:

$R_1$ represents methyl;
$R_2$ represents hydrogen;
$R_3$ represents hydrogen;
Ar represents 2-fluorophenyl, 2,4-dichlorophenyl, 2,4-difluorophenyl, 4-(trifluoromethyl)phenyl or 4-chlorophenyl;
A represents a benzene ring or a 5- or 6-membered heterocyclic ring containing one or more heteroatoms selected from N, O and S, wherein A can be unsubstituted or have 1, 2, 3 or 4 groups W; and
the stereochemistry of the compounds is (1R,2R).

A still more preferred class of compounds of formula I is that wherein:

$R_1$ represents methyl;
$R_2$ represents hydrogen;
$R_3$ represents hydrogen;
Ar represents 2-fluorophenyl, 2,4-dichlorophenyl, 2,4-difluorophenyl, 4-(trifluoromethyl)phenyl or 4-chlorophenyl;
A represents a benzene ring or a 5-membered heterocyclic ring containing one heteroatom selected from N, O and S or two heteroatoms selected from the pairs N/N, N/O and N/S, wherein A can be unsubstituted or have 1, 2, 3 or 4 groups W; and
the stereochemistry of the compounds is (1R,2R).

A particularly preferred class of compounds of formula I are those compounds of formula Ia

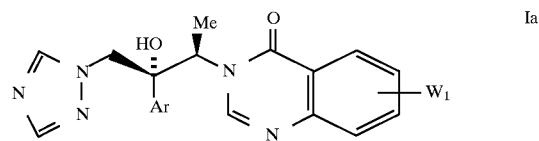

wherein:
Ar represents 2-fluorophenyl, 2,4-dichlorophenyl, 2,4-difluorophenyl, 4-(trifluoromethyl)phenyl or 4-chlorophenyl;
$W_1$ represents 1, 2, 3 or 4 groups independently selected from hydrogen, $C_1$–$C_4$ haloalkyl, $C_1$–$C_4$ haloalkoxy, halogen, cyano, a group —C(=NR$_4$)NHR$_7$, a group —C(=NR$_7$)OR$_4$, and moreover one of the groups $W_1$ can also represent a group —X—R$_8$ or a group of formula (i)–(iv), wherein $W_1$ can be on any available position of the benzene ring; and
the stereochemistry of the compounds is (1R,2R).

Another particularly preferred class of compounds of formula I are those compounds of formula Ib

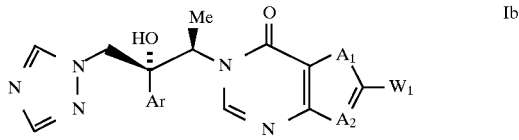

wherein:
Ar represents 2-fluorophenyl, 2,4-dichlorophenyl, 2,4-difluorophenyl, 4-(trifluoromethyl)phenyl or 4-chlorophenyl;
$A_1$ is S, O or NMe;
$A_2$ is CH, CMe or N;
$W_1$ represents hydrogen, halogen, $C_1$–$C_4$ haloalkyl, $C_1$–$C_4$ haloalkoxy, cyano, a group —C(=NR$_4$)NHR$_7$, a group —C(=NR$_7$)OR$_4$, or a group —R$_8$; and the stereochemistry of the compounds is (1R,2R).

A specially preferred group of compounds within compounds of formula Ib are those compounds represented by the formula

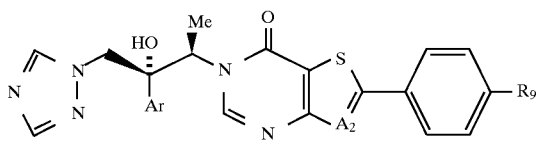

wherein:
Ar represents 2-fluorophenyl, 2,4-dichlorophenyl, 2,4-difluorophenyl, 4-(trifluoromethyl)phenyl or 4-chlorophenyl;
$A_2$ is CH, CMe or N;
$R_9$ is halogen, $C_1$–$C_4$ haloalkyl, $C_1$–$C_4$ haloalkoxy, cyano, nitro, a group —$SO_2R_6$, a group —$C(=NR_4)NHR_7$, or a group —$C(=NR_7)OR_4$; and
the stereochemistry of the compounds is (1R,2R).

The compounds of formula I contain one or more basic nitrogen atoms and, consequently, they can form salts with acids, which are also included in the present invention. There is no limitation on the nature of these salts, provided that, when used for therapeutic purposes, they are pharmaceutically acceptable, which, as is well-known in the art, means that they do not have reduced activity (or unacceptable reduced activity) or increased toxicity (or unacceptable increased toxicity) compared with the free compounds. Examples of these salts include: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid, maleic acid; and other mineral and carboxylic acids well known to those skilled in the art. The salts are prepared by reacting the free base with a sufficient amount of the desired acid to produce a salt in the conventional manner. Free bases and their salts differ in certain physical properties, such as solubility, but they are equivalent for the purposes of the invention.

Some compounds of the present invention can exist in solvated form, including hydrated forms. In general, the solvated forms, with pharmaceutically acceptable solvents such as water, ethanol and the like, are equivalent to the unsolvated forms for the purposes of the invention.

The compounds of formula I contain one or more asymmetric carbons and, consequently, can exist as different stereoisomers. The present invention covers both each of the individual stereoisomers and their mixtures. When $R_1$ is $C_1$–$C_4$ alkyl and $R_2$ is hydrogen, those compounds of formula I wherein the absolute configuration of the carbon atoms to which the Ar and $R_1$ groups are bonded is (R,R) are preferred, i.e. compounds of formula:

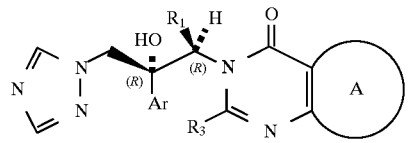

Diastereoisomers can be separated by conventional techniques such as chromatography or fractional crystallization. The optical isomers can be resolved using any of the conventional techniques of optical resolution to give optically pure isomers. Such a resolution can be performed in any chiral synthetic intermediate as well as in the products of general formula I. The optically pure isomers can also be individually obtained using enantiospecific synthesis. We have obtained the optically pure (R,R) isomers starting from optically pure amine II, prepared following the general procedure described in *J. Org. Chem*, 1995, 60, 3000–3012. As stated above, the present invention covers the individual isomers as well as their mixtures (e.g. racemic mixtures), whether as obtained by synthesis or by physically mixing them up.

Some of the compounds of formula I may present tautomerism. For example, when the compounds of the present invention contain an amidino group of formula —$C(=NR_4)$$NHR_7$, the following tautomeric structures may exist in equilibrium:

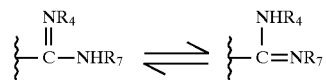

all of which are encompassed by the present invention.

The compounds of formula I can be prepared using the procedures described below. The precise method used for the preparation of a given compound may vary depending on its chemical structure.

In general, compounds of formula I can be prepared by reacting an amine of formula II first with an acid of formula III in the presence of a an appropriate condensing agent, for example dicyclohexylcarbodiimide, alone or in combination with 1-hydroxybenzotriazole, in a polar solvent, such as a substituted amide (for example N-methylpyrrolidone or dimethylformamide), an ether (for example tetrahydrofuran or dioxane) or diglyme, at a temperature preferably comprised between 0° C. and 100° C., and then with a reactive derivative of an acid $R_3CO_2H$, such as its alkyl imidate (for example the methyl or ethyl imidate), its amidine, its acid chloride, its anhydride or its orthoester, at a temperature that favours the elimination of water, alcohol or ammonia (depending on the case), generally above 50° C. If desired, it is also possible to use the acid $R_3CO_2H$ as such; in this case it is necessary to use two equivalents of the dehydrating agent.

Alternatively, some compounds of formula I may also be obtained by reaction of an amine of formula II with a compound of formula IV in a polar solvent, such as a substituted amide (for example N-methylpyrrolidone or dimethylformamide) or an ether (for example tetrahydrofuran), at a temperature preferably between room temperature and that of the refluxing solvent. Compounds of formula IV can be obtained by reacting a compound of formula III with an anhydride $(R_3CO)_2O$ or, when in a compound of formula IV $R_3$ is hydrogen, by reacting the N-formyl derivative of III with a dehydrating agent such as dicyclohexylcarbodiimide or acetic anhydride.

Moreover, some compounds of formula I can also be prepared by interconversion from another compound of formula I in one or a plurality of steps.

Thus, it is possible to use a group W to generate other groups W by reactions well known in organic chemistry, such as the reactions listed below. These reactions are mentioned here only as illustrative examples of the several procedures which can be used to interconvert compounds of the present invention and are not intended to limit the scope of the preparation of compounds of formula I in any way. For example, a nitro group can be reduced to an amino group, for example by hydrogenation in the presence of a catalyst such as Pd/C in a suitable solvent such as an alcohol, for example ethanol, at a temperature between room temperature and that of the refluxing solvent and at a pressure preferably between atmospheric pressure and 10 atm. A thioether group can be oxidized to a sulfinyl or sulfonyl group by treatment with a suitable oxidising agent. For example, a thioether group can be oxidized to a sulfonyl group by treatment with m-chloroperbenzoic acid in a suitable solvent such as a halogenated hydrocarbon at a temperature preferably between 0° C. and room temperature. An amino group can be acylated by treatment for example with an anhydride, such as acetic anhydride or trifluoroacetic anhydride, under the usual conditions. Moreover, an amino group can be converted to a group of formula (i) by treatment with phenyl chloroformate, subsequent reaction of the phenyl carbamate thus obtained with hydrazine and finally cyclisation of the resulting semicarbazide with formamidine or acetamidine in a suitable solvent such as dimethylformamide at a temperature between room temperature and that of the refluxing solvent. A nitrite group can be converted to a tetrazole group by treatment with a suitable azide such as sodium azide or ammonium azide (which may be prepared in situ from sodium azide and ammonium chloride) in a suitable solvent such as a polar solvent, for example dimethylformamide or N-methylpyrrolidone, at a temperature preferably between room temperature and that of the refluxing solvent. Another example of interconversion is the N-alkylation of a group of formula (i) or a tetrazole by treatment with the corresponding alkyl halide in the presence of a base such as potassium or cesium carbonate in a suitable aprotic solvent such as dimethylformamide. An amino group can also be converted to a bromo or iodo atom by treatment with sodium nitrite in the presence of an acid such as hydrobromic or hydrochloric acid in a suitable solvent such as water at a temperature preferably comprised between −15° and +10° C. to give the corresponding diazonium salt and subsequent reaction with CuBr or KI respectively, at a temperature comprised between room temperature and that of the refluxing solvent. A nitrite group can also be converted to a carbamoyl group by bubbling HCl gas in an alcohol, such as methanol, to give the intermediate alkyl imidate, and subsequently treating this alkyl imidate with aqueous HCl. An alkyl imidate group can also be converted to an amino(imino)methyl group by reaction with an amine using the corresponding alkanol as solvent. Moreover, a halogen atom, for example bromo or iodo, can be converted to an aromatic group of formula —$R_8$ by a coupling reaction between the corresponding haloderivative and a boronic acid or ester of formula (RO)$_2$B—$R_8$ (wherein R represents hydrogen or $C_{1-4}$ alkyl) in the presence of a palladium catalyst such as Pd(OAc)$_2$ or Pd(PPh$_3$)$_4$ in a suitable solvent such as dimethoxyethane at a temperature preferably between room temperature and that of the refluxing solvent.

Moreover, when W represents a fluorine atom, this can be used to introduce a great variety of new groups W by substitution reactions. As examples of these reactions we can mention: the conversion into a $C_1$–$C_4$ alkoxy, $C_1$–$C_4$ haloalkoxy, —$OR_8$, —$SR_6$ or —$SR_8$ group by treatment with an alkaline metal salt of the corresponding alcohol o thiol, for example the sodium salt, in a suitable aprotic solvent such as N-methylpyrrolidone at a temperature between room temperature and that of the refluxing solvent; the introduction of a triazole or an imidazole group, by treatment of the fluoroderivative with the sodium salt of triazole or imidazole in the same experimental conditions; the conversion into an amine (—$NR_4R_5$, 1-pyrrolidine, morpholine, —$NR_4R_8$, a group of formula (ii) or a group of formula (iii)) by treatment with the corresponding amine in a suitable aprotic solvent such as N-methylpyrrolidone at a temperature between room temperature and that of the refluxing solvent.

Similar procedures can be used when W represents a group —X—$R_8$ to modify the substituents $R_9$ on the phenyl ring $R_8$.

Amines of formula II can be prepared as described in *Chem. Pharm. Bull.*, 1990, 38(9), 2476–2486, or in *J. Org. Chem*, 1995, 60, 3000–3012.

Acids of formula III and of formula $R_3$COOH or derivatives thereof are commercially available, widely described in the literature or can be prepared by methods analogous to those known in the art. For example, 1-aryl-5-aminopyrazole-4-carboxylic acids can be prepared by reacting ethyl ethoxymethylenecyanoacetate with the corresponding arylhydrazine, followed by hydrolysis under basic conditions, according to the procedure described in *Bull. Soc. Chim. Fr.*, 1970, 7, 2717. 5-Aryl-3-aminothiophene-2-carboxylic acids can be prepared by reacting a suitable β-chlorocinnamonitrile with ethyl thioglycolate in the presence of a base, followed by alkaline hydrolysis, as described in *Synthesis*, 1984, 275.

According to the activity of the compounds of formula I, the present invention further provides compositions that contain a compound of the present invention, together with an excipient and optionally other auxiliary agents, if necessary. The compounds of the present invention can be administered in different pharmaceutical preparations, the precise nature of which will depend, as it is well known, upon the chosen route of administration and the nature of the pathology to be treated.

Thus, solid compositions according to the present invention for oral administration include compressed tablets, dispersible powders, granules and capsules. In tablets, the active component is admixed with at least one inert diluent such as lactose, starch, mannitol, microcrystalline cellulose or calcium phosphate; granulating and disintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated tablets can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides. Soft gelatin capsules are also possible wherein the active ingredient is mixed with water or an oily medium, for example peanut oil, liquid paraffin or olive oil.

Dispersible powders and granules suitable for the preparation of a suspension by the addition of water provide the active ingredient in admixture with a dispersing or wetting agent; a suspending agent, such as sodium carboxymethylcellulose, methylcellulose, hydroxypropylmethylcellulose, sodium alginate, polyvinylpirrolidone, gum tragacanth, xantham gum, gum acacia, and one or more preservatives, such as methyl or n-propyl p-hydroxybenzoate. Additional excipients, for example sweetening, flavoring and coloring agents may also be present.

Liquid compositions for oral administration include emulsions, solutions, suspensions, syrups and elixirs containing commonly used inert diluents, such as distilled water, ethanol, sorbitol, glycerol, or propylene glycol. Aqueous solutions can also be prepared using β-cyclodextrins, such as hydroxypropyl-β-cyclodextrin. Such compositions may also comprise adjuvants such as wetting agents, suspending agents, sweetening, flavoring, perfuming, preserving agents and buffers.

Other compositions for oral administration include spray compositions, which may be prepared by known methods. The spray compositions will contain a suitable propellant.

Preparations for injection, according to the present invention, for parenteral administration include sterile aqueous or non-aqueous solutions, suspensions or emulsions, in a non-toxic parentally-acceptable diluent or solvent. Examples of aqueous solvents or suspending media are distilled water for injection, Ringer's solution, and isotonic sodium chloride solution. Aqueous solutions can also be prepared using β-cyclodextrins, such as hydroxypropyl-β-cyclodextrin. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by one of the known methods or manufactured in the form of sterile solid compositions which can be dissolved in sterile water or some other sterile injectable medium immediately before use. When all of the components are sterile, the injectables will maintain the sterility if they are manufactured in sterile environment.

Preparations for vaginal administration according to the present invention include tablets, capsules, softgels, moulded pessaries, creams, foams and vaginal douches. Vaginal tablets provide the active component in admixture with lactose, microcrystalline cellulose, pregelatinized starch, polyvidone and magnesium stearate as typical excipients. Soft gelatin capsules (softgels) can be made dispersing the active ingredient in an oily medium, for example liquid paraffin, dimethylpolysiloxane 1000 or hydrogenated soybean oil. Moulded pessaries provide the active ingredient in admixture with a suitable synthetic or semisynthetic base (such as Suppocire® or Novata® types). Low viscosity saturated $C_8$ to $C_{12}$ fatty acid glycerides and colloidal silice are also added to improve incorporation and to prevent sedimentation of the active ingredient. Vaginal creams can be prepared as emulsions, with sufficient viscosity to retain their integrity and adhere to the vaginal cavity. Neutral fats, fatty acids, waxes, mineral oils and fatty acid esters can be used as the oily phase. Water, glycerine, sorbitol solution and polyethylene glycol are suitable excipients for the aqueous phase. Non-ionic emulsifying agents like polyethylene glycol ethers may also be used, and such compositions may also contain preserving, buffering and stiffening agents. Foaming systems can be made using a foamer (dispenser) that is able to transform a solution into a foam. Such systems may include cosolvents, buffers, preservatives, foam stabilizers and perfumes in an aqueous vehicle. Vaginal douches may contain cosolvents, preservatives, buffers and perfuming agents in a surfactant rich aqueous solution.

A compound of the invention may also administered in the form of suppositories for rectal administration of the drug, or as creams, ointments, pastes, lotions, gels, sprays, foams, aerosols, solutions, suspensions or powders for topical use. Such compositions are prepared following conventional procedures well known to those skilled in the art.

A compound of the invention may also be administered as a hair or body shampoo. These formulations may be prepared using suitable ionic and/or amphoteric surface-active agents such as sodium laureth sulfate, triethanolamine laureth sulfate, cocoamidopropyl betaine; thickening agents for example cocamide DEA, carbomer, sodium chloride and polyethylene glycol 6000 distearate; and optionally, emolient and superfatting agents, buffers, and preserving and perfuming agents.

The dosage and frequency of dose may vary depending upon the nature and severity of the fungal disease, symptoms, age and body weight of the patient, as well as upon the route of administration. In general, the compounds of the invention will be administered orally or parenterally at a dosage ranging from 0.01 mg/Kg/day to 100 mg/Kg/day, which can be administered as a single dose or as divided doses.

Following are some representative preparations for tablets, capsules, syrups, aerosols and injectables. They can be prepared following standard procedures and they are useful in the treatment of fungal diseases.

| Tablets | |
|---|---|
| Compound of formula I | 100 mg |
| Dibasic calcium phosphate | 125 mg |
| Sodium starch glycolate | 10 mg |
| Talc | 12.5 mg |
| Magnesium stearate | 2.5 mg |
| | 250.0 mg |
| Hard gelatin capsules | |
| Compound of formula I | 100 mg |
| Lactose | 197 mg |
| Magnesium stearate | 3 mg |
| | 300 mg |
| Syrup | |
| Compound of formula I | 0.4 g |
| Sucrose | 45 g |
| Flavouring agent | 0.2 g |
| Sweetening agent | 0.1 g |
| Water to | 100 mL |
| Aerosol | |
| Compound of formula I | 4 g |
| Flavouring agent | 0.2 g |
| Propylene glycol to | 100 mL |
| Suitable propellent to | 1 unit |
| Injectable preparation 1 | |
| Compound of formula I | 100 mg |
| Benzylic alcohol | 0.05 mL |
| Propylene glycol | 1 mL |
| Water to | 5 mL |
| Injectable preparation 2 | |
| Compound of formula I | 100 mg |
| Hydroxypropyl-β-cyclodextrin | 1 g |
| Sodium chloride | 90 mg |
| Water to | 10 mL |

The following examples illustrate, but do not limit, the scope of the present invention.

EXAMPLE 1

(1R,2R)-7-Chloro-3-[2-(2,4-difluorophenyl)-2-hydroxy-1-methyl-3-(1H-1,2,4-triazol-1-yl)propyl] quinazolin-4(3H)-one To a solution of (2R,3R)-3-amino-2-(2,4-difluorophenyl)-1-(1H-1,2,4-triazol-1-yl)-2-butanol (250 mg, 0.93 mmol) (obtained as described in Bartroli et al *J. Org. Chem,* 1995, 60, 3000–3012) in NMP (5 mL) was added HOBT (132 mg, 0.98 mmol, 1.05 eq). Next, 4-chloroanthranilic acid (160 mg, 0.93 mmol, 1 eq) and DCC (202 mg, 0.98 mmol, 1.05 eq) was added and the mixture was stirred at room temperature for 18 h. Then, formamidine acetate (437 mg, 4.19 mmol, 4.5 eq) was added and the mixture was heated at 130° C. for 24 h. Water (75 mL) was added and the solid formed was collected by filtration and was then partitioned between aqueous 1N NaOH solution and EtOAc. The aqueous phase was discarded and the organic phase was washed with brine, dried over $Na_2SO_4$, filtered, concentrated and the residue purified by flash chromatography (hex: EtOAc 1:5) and recrystallized from a EtOAc: hexane: ether mixture to give the title product (268 mg, 67%) as a white solid: mp 116°–122° C.; $^1$H NMR (80 MHz, $CDCl_3$) δ (TMS) 8.57 (s, 1H, N=CH—N), 8.26 (d, J=8.5Hz, 1H, arom), 7.74 (s, 2H, triazole), 7.7–7.3 (m, 3H, arom), 6.9–6.7 (m, 2H, arom), 5.91 (dq, $J_d$=2, $J_q$=7, 1H, MeCH), 5.53 (d, J=2, 1H, OH), 5.14 (d, J=14, 1H, CH(H)), 4.00 (d, J=14, 1H, CH(H)), 1.29 (d, J=7, 3H, CHMe); GC/MS 224 (Tr—$CH_2$COHAr, $C_{10}H_8F_2N_3O$), 207 (N-ethylheterocycle, $C_{10}H_9ClN_2O$); $[a]_D$=−7.9° (c 1, $CHCl_3$). Analysis calculated for $C_{20}H_{16}ClF_2N_5O_2$: C 55.63; H 3.73; N 16.22. Found: C 55.23; H 4.09; N 16.13.

EXAMPLE 2

(1R,2R)-7-Cyano-3-[2-(2,4-difluorophenyl)-2-hydroxy-1-methyl-3-(1H-1,2,4-triazol-1-yl)propyl] quinazolin-4(3H)-one Following a similar procedure to that described in example 1 but using 4-cyanoanthranilic acid (prepared as described in Chan et al. *J. Am. Chem. Soc.* 1977, 99, 6721) the title compound was obtained as a white solid: mp 168°–169° C.; $^1$H NMR (300 MHz, $CDCl_3$) δ (TMS) 8.64 (s, 1H, N=CH—N), 8.43 (d, J=8.2, 1H, arom), 8.08 (d, J=1.1, 1H, arom), 7.76 (s, 1H, triazole), 7.74 (s, 1H, triazole), 7.73 (dd, J=1.5, J=8.2, 1H, arom), 7.47 (dt, $J_d$=6.4, $J_t$=8.8, 1H, arom), 6.9–6.8 (m, 2H, arom), 5.91 (dq, $J_d$=1.2, $J_q$=7.3, 1H, MeCH), 5.60 (d, J=1.3, 1H, OH), 5.13 (d, J=14.1, 1H, CH(H)), 4.00 (d, J=14.1, 1H, CH(H)), 1.31 (d, J=7.3, 3H, CHMe); GC/MS 423 (M$^+$+1), 198 ($C_{11}H_8N_3O$), 224 ($C_{10}H_8F_2N_3O$); $[α]_D$=−0.95° (c 1, $CHCl_3$). Analysis calculated for $C_{21}H_{16}F_2N_6O_2$: C 59.71; H 3.82; N 19.90. Found: C 59.68; H 3.4.15; N 19.56.

EXAMPLE 3

(1R,2R)-3-[2-(2,4-Difluorophenyl)-2-hydroxy-1-methyl-3-(1H-1,2,4-triazol-1-yl)propyl]-7-dimethylaminoquinazolin-4(3H)-one Following a similar procedure to that described in example 1 but using 4-fluoroanthranilic acid and DMF as solvent the title compound was obtained as a white solid: mp 201°–201° C.; $^1$H NMR (80 MHz, $CDCl_3$) δ (TMS) 8.45 (s, 1H, N=CH—N), 8.15 (d, J=8, 1H, arom), 7.75 (s, 1H, triazole), 7.72 (s, 1H, triazole), 7.7–7.3 (m, arom), 7.1–6.5 (m, arom), 5.92 (dq, $J_d$=2, $J_q$=7.3, 1H, MeCH), 5.43 (d, J=2, 1H, OH), 5.18 (d, J=14, 1H, CH(H)), 4.05 (d, J=14, 1H, CH(H)), 3.11 (s, 6H, $NMe_2$), 1.27 (d, J=7.3, 3H, CHMe); GC/MS 440 (M$^+$), 216 ($C_{12}H_{14}N_3O$), 224 ($C_{10}H_8F_2N_3O$); $[α]_D$=−43° (c 1, $CHCl_3$). Analysis calculated for $C_{22}H_{22}F_2N_6O_2$: C 59.99; H 5.03; N 19.08. Found: C 60.07; H 5.32; N 18.88.

EXAMPLE 4

(1R,2R)-3-[2-(2,4-Difluorophenyl)-2-hydroxy-1-methyl-3-(1H-1,2,4-triazol-1-yl)propyl]-7-dimethylamino-6-fluoroquinazolin-4(3H)-one Following a similar procedure to that described in example 1 but using 4,5-difluoroanthranilic acid and DMF as solvent the title compound was obtained as a white solid: mp 197°–198° C.; $^1$H NMR (80 MHz, $CDCl_3$) δ (TMS) 8.45 (s, 1H, N=CH—N), 7.91 (s, 1H, arom), 7.74 (broad s, 3H, triazole, arom), 7.7–7.3 (m, 1H, arom), 7.0–6.6 (m, 2H, arom), 5.90 (dq, $J_d$=1.5, $J_q$=7.3, 1H, MeCH), 5.46 (d, J=1.5, 1H, OH), 5.16 (d, J=14, 1H, CH(H)), 4.00 (d, J=14, 1H, CH(H)), 3.06 (s, 6H, $NMe_2$), 1.25 (d, J=7.3, 3H, CHMe); MS 458 (M$^+$); $[α]_D$=−36° (c 1, $CHCl_3$). Analysis calculated for $C_{22}H_{21}F_3N_6O_2$·1/2 $Et_2O$: C 57.64; H 4.62; N 18.33. Found: C 57.59; H 4.82; N 18.01.

EXAMPLE 5

(1R,2R)-3-[2-(2,4-Difluorophenyl)-2-hydroxy-1-methyl-3-(1H-1,2,4-triazol-1-yl)propyl]quinazolin-4 (3H)-one Following a similar procedure to that described in example 1 but using anthranilic acid the title compound was obtained: mp 122°–128° C.; $^1$H NMR (80 MHz, $CDCl_3$) δ (TMS) 8.59 (s, 1H, N=CH—N), 8.35 (d, J=8.5, 1H, arom), 8.0–7.4 (m, 6H, triazole, arom), 6.9–6.7 (m, 2H, arom), 5.95 (dq, $J_d$=1.6, $J_q$=7.1H, MeCH), 5.50 (d, J=1.6, 1H, OH), 5.18 (d, J=14, 1H, CH(H)), 4.02 (d, J=14, 1H, CH(H)), 1.31 (d, J=7, 3H, CHMe); $[α]_D$=−2.9° (c 1, $CHCl_3$). Analysis calculated for $C_{20}H_{17}F_2N_5O_2$: C 60.45; H 4.31; N 17.62. Found: C 59.84; H 4.36; N 16.97.

EXAMPLE 6

(1R,2R)-8-Chloro-3-[2-(2,4-difluorophenyl)-2-hydroxy-1-methyl-3-(1H-1,2,4-triazol-1-yl)propyl] quinazolin-4(3H)-one Following a similar procedure to that described in example 1 but using 3-chloroanthranilic acid the title compound was obtained as a white solid: mp 110°–113° C.; $^1$H NMR (80 MHz, $CDCl_3$) δ (TMS) 8.73 (s, 1H, N=CH—N), 8.27 (dd, J=1.5, J=8, 1H, arom), 7.84 (dt, $J_d$=1.5, $J_t$=7.7, 1H, arom), 7.74 (broad s, 2H, triazole), 7.7–7.3 (m, 2H, arom), 7.0–6.6 (m, 2H, arom), 5.90 (dq, $J_d$=1.5, $J_q$=7.3, 1H, MeCH), 5.55 (d, J=1.5, 1H, OH), 5.15 (d, J=14, 1H, CH(H)), 4.00 (d, J=14, 1H, CH(H)), 1.30 (d, J=7.3, 3H, CHMe); $[α]_D$=−21.8° (c 1, $CHCl_3$). Analysis calculated for $C_{20}H_{16}ClF_2N_5O_2$: C 55.63; H 3.73; N 16.22. Found: C 55.92; H 3.76; N 15.88.

EXAMPLE 7

(1R,2R)-6-Chloro-3-[2-(2,4-difluorophenyl)-2-hydroxy-1-methyl-3-(1H-1,2,4-triazol-1-yl)propyl] quinazolin-4(3H)-one Following a similar procedure to that described in example 1 but using 5-chloroanthranilic acid the title compound was obtained as a white solid: mp 188°–189° C.; $^1$H NMR (80 MHz, $CDCl_3$) δ (TMS) 8.56 (s, 1H, N=CH—N), 8.30 (t, J=1.3, 1H, arom), 7.75–7.70 (m, 3H, triazole, arom), 7.7–7.3 (m, 2H, arom), 7.0–6.6 (m, 2H, arom), 5.93 (dq, $J_d$=1.5, $J_q$=7.3, 1H, MeCH), 5.52 (d, J=1.5, 1H, OH), 5.15 (d, J=14, 1H, CH(H)), 3.98 (d, J=14, 1H, CH(H)), 1.30 (d, J=7.3, 3H, CHMe); $[α]_D$=+14.6° (c 1, $CHCl_3$). Analysis calculated for $C_{20}H_{16}ClF_2N_5O_2$: C 55.63; H 3.73; N 16.22. Found: C 55.65; H 3.75; N 16.10.

EXAMPLE 8

(1R,2R)-5Chloro-3-[2-(2,4-difluorophenyl)-2-hydroxy-1-methyl-3-(1H-1,2,4-triazol-1-yl)propyl] quinazolin-4(3H)-one Following a similar procedure to that described in example 1 but using 6-chloroanthranilic acid the title compound was obtained as a white solid: mp 114°–119° C.; $^1$H NMR (300 MHz, CDCl$_3$) δ (TMS) 8.59 (s, 1H, N=CH—N), 7.79 (s, 1H, triazole), 7.76 (s, 1H, triazole), 7.8–7.5 (m, 3H, arom), 7.50 (dt, J$_d$=6.4, J$_t$=8.8, 1H, arom), 6.9–6.7 (m, 2H, arom), 5.95 (dq, J$_d$=1.7, J$_q$=7.3, 1H, MeCH), 5.58 (d, J=1.7, 1H, OH), 5.23 (d, J=14.2, 1H, CH(H)), 4.08 (d, J=14.2, 1H, CH(H)), 1.29 (d, J=7.3, 3H, CHMe); [α]$_D$=+39.5° (CHCl$_3$, c 1). Analysis calculated for C$_{20}$H$_{16}$ClF$_2$N$_5$O$_2$: C 55.63; H 3.73; N 16.22. Found: C 55.41; H 3.87; N 15.51.

EXAMPLE 9

(1R,2R)-6,8Dichloro-3-[2-(2,4-difluorophenyl)-2-hydroxy-1-methyl-3-(1H-1,2,4-triazol-1-yl)propyl]quinazolin4(3H)-one Following a similar procedure to that described in example 1 but using 3,5-dichloroanthranilic acid the title compound was obtained as a white solid: mp 158°–160° C.; $^1$H NMR (80 MHz, CDCl$_3$) δ (TMS) 8.71 (s, 1H, N=CH—N), 8.24 (d, J=2.2, 1H, arom), 7.92 (d, J=2.2, 1H, arom), 7.75 (s, 2H, triazole), 7.6–7.1 (m, 1H, arom), 7.0–6.6 (m, 2H, arom), 5.90 (dq, J$_d$=1.5, J$_q$=7.3, 1H, MeCH), 5.58 (d, J=1.5, 1H, OH), 5.12 (d, J=14, 1H, CH(H)), 3.99 (d, J=14, 1H, CH(H)), 1.30 (d, J=7.3, 3H, CHMe); [α]$_D$=−6.8° (c 1, CHCl$_3$). Analysis calculated for C$_{20}$H$_{15}$Cl$_2$F$_2$N$_5$O$_2$: C 51.52; H 3.24; N 15.02. Found: C 51.60; H 3.24; N 14.74.

EXAMPLE 10

(1R,2R)-6-Bromo-3-[2-(2,4-difluorophenyl)-2-hydroxy-1-methyl-3-(1H-1,2,4-triazol-1-yl)propyl]quinazolin4(3H)-one Following a similar procedure to that described in example 1 but using 5-bromoanthranilic acid the title compound was obtained as a white solid: mp 182°–183° C.; $^1$H NMR (300 MHz, CDCl$_3$) δ (TMS) 8.59 (s, 1H, N=CH—N), 8.47 (d, J=2.2, 1H, arom), 7.88 (dd, J=2, J=8.6, 1H, arom), 7.78 (s, 1H, triazole), 7.74 (s, 1H, triazole), 7.64 (d, J=8.6, 1H, arom), 7.48 (dt, J$_d$=6.5, J$_t$=8.8, 1H, arom), 6.9–6.7 (m, 2H, arom), 5.93 (dq, J$_d$=1.7, J$_q$=7.3, 1H, MeCH), 5.54 (d, J=1.7, 1H, OH), 5.16 (d, J=14.1, 1H, CH(H)), 4.01 (d, J=14.1, 1H, CH(H)), 1.31 (d, J=7.3, 3H, CHMe); [α]$_D$=+15.9° (c 1, CHCl$_3$). Analysis calculated for C$_{20}$H$_{16}$BrF$_2$N$_5$O$_2$: C 50.44; H 3.39; N 14.70. Found: C 50.47; H 3.55; N 14.60.

EXAMPLE 11

(1R,2R)-6,8-Dibromo-3-[2-(2,4-difluorophenyl)-2-hydroxy-1-methyl-3-(1H-1,2,4-triazol-1-yl)propyl]quinazolin-4(3H)-one Following a similar procedure to that described in example 1 but using 3,5-dibromoanthranilic acid the title compound was obtained as a white solid: mp 134°–135° C.; $^1$H NMR (300 MHz, CDCl$_3$) δ (TMS) 8.75 (s, 1H, N=CH—N), 8.46 (d, J=2, 1H, arom), 8.20 (d, J=2, 1H, arom), 7.78 (s, 1H, triazole), 7.76 (s, 1H, triazole), 7.49 (dt, J$_d$=6.5, J$_t$=8.8, 1H, arom), 6.9–6.7 (m, 2H, arom), 5.90 (dq, J$_d$=1.7, J$_q$=7.3, 1H, MeCH), 5.58 (d, J=1.6, 1H, OH), 5.13 (d, J=14.1, 1H, CH(H)), 4.00 (d, J=14.1, 1H, CH(H)), 1.31 (d, J=7.3, 3H, CHMe); [α]$_D$=−10.2° (c 1, CHCl$_3$). Analysis calculated for C$_{20}$H$_{15}$Br$_2$F$_2$N$_5$O$_2$: C 43.27; H 2.72; N 12.61. Found: C 43.55; H 2.69; N 12.52.

EXAMPLE 12

(1R,2R)-3-[2-(2,4-Difluorophenyl)-2-hydroxy-1-methyl-3-(1H-1,2,4-triazol-1-yl)propyl]-7-fluoroquinazolin-4(3H)-one Following a similar procedure to that described in example 1 but using 4-fluoroanthranilic acid the title compound was obtained as a white solid: mp 106°–107° C.; $^1$H NMR (300 MHz, CDCl$_3$) δ (TMS) 8.60 (s, 1H, N=CH—N), 8.37 (dd, J=6.0, J=8.9, 1H, arom), 7.78 (s, 1H, triazole), 7.75 (s, 1H, triazole), 7.49 (dt, J$_d$=6.5, J$_t$=8.7, 1H, arom), 7.42 (dd, J=2.4, J=9.4, 1H, arom), 7.27 (dt, J$_d$=2.5, J$_t$=8.7, 1H, arom), 6.9–6.7 (m, 2H, arom), 5.94 (dq, J$_d$=1.7, J$_q$=7.3, 1H, MeCH), 5.54 (d, J=1.7, 1H, OH), 5.17 (d, J=14.1, 1H, CH(H)), 4.03 (d, J=14.1, 1H, CH(H)), 1.31 (d, J=7.3, 3H, CHMe); [α]$_D$=−2.0° (c 1, CHCl$_3$). Analysis calculated for C$_{20}$H$_{16}$F$_3$N$_5$O$_2$: C 57.83; H 3.88; N 16.86. Found: C 57.38; H 4.04; N 16.87.

EXAMPLE 13

(1R,2R)-3-[2-(2,4-Difluorophenyl)-2-hydroxy-1-methyl-3-(1H-1,2,4-triazol-1-yl)propyl]-5fluoroquinazolin-4(3H)-one Following a similar procedure to that described in example 1 but using 6-fluoroanthranilic acid the title compound was obtained as a white solid: mp 94°–122° C.; $^1$H NMR (300 MHz, CDCl$_3$) δ (TMS) 8.57 (s, 1H, N=CH—N), 7.78 (s, 1H, triazole), 7.75 (s, 1H, triazole), 7.73 (dd, J=8.2, J=1.5, 1H, arom), 7.8–7.5 (m, 1H, arom), 7.49 (dt, J$_d$=6.4, J$_t$=8.8, 1H, arom), 7.20 (ddd, J=1.0, J=8.0, J=10.7, 1H, arom), 6.9–6.7 (m, 2H, arom), 5.96 (dq, J$_d$=1.7, J$_q$=7.3, 1H, MeCH), 5.57 (d, J=1.7, 1H, OH), 5.23 (d, J=14.2, 1H, CH(H)), 4.07 (d, J=14.2, 1H, CH(H)), 1.30 (d, J=7.3, 3H, CHMe); [α]$_D$=+18.1° (c 1, CHCl$_3$). Analysis calculated for C$_{20}$H$_{16}$F$_3$N$_5$O$_2$: C 57.83; H 3.88; N 16.86. Found: C 57.53; H 3.71; N 16.61.

EXAMPLE 14

(1R,2R)-3-[2-(2,4-Difluorophenyl)-2-hydroxy-1-methyl-3-(1H-1,2,4-triazol-1-yl)propyl]-6-fluoroquinazolin-4(3H)-one Following a similar procedure to that described in example 1 but using 5-fluoroanthranilic acid the title compound was obtained as a white solid: mp 192°–193° C.; $^1$H NMR (300 MHz, CDCl$_3$) δ (TMS) 8.57 (s, 1H, N=CH—N), 7.98 (dd, J=2.4, J=8.4, 1H, arom), 7.78 (s, 1H, triazole), 7.75 (s, 1H, triazole), 7.8–7.7 (m, 1H, arom), 7.6–7.4 (m, 2H, arom), 6.9–6.7 (m, 2H, arom), 5.95 (dq, J$_d$=1.7, J$_q$=7.3, 1H, MeCH), 5.55 (d, J=1.7, 1H, OH), 5.17 (d, J=14.2, 1H, CH(H)), 4.02 (d, J=14.2, 1H, CH(H)), 1.31 (d, J=7.3, 3H, CHMe); [α]$_D$=−2.3° (c 1, CHCl$_3$). Analysis calculated for C$_{20}$H$_{16}$F$_3$N$_5$O$_2$: C 57.83; H 3.88; N 16.86. Found: C 58.16; H 3.88; N 16.65.

EXAMPLE 15

(1R,2R)-6,7-Difluoro-3-[2-(2,4-difluorophenyl)-2-hydroxy-1-methyl-3-(1H-1,2,4-triazol-1-yl)propyl]quinazolin-4(3H)-one Following a similar procedure to that described in example 1 but using 4,5-difluoroanthranilic acid the title compound was obtained as a white solid: mp 212°–213° C.; $^1$H NMR (300 MHz, CDCl$_3$) δ (TMS) 8.56 (s, 1H, N=CH—N), 8.09 (dd, J=8.4, J=9.9, 1H, arom), 7.77 (s, 1H, triazole), 7.74 (s, 1H, triazole), 7.54 (dd, J=7.0, J=9.9, 1H, arom), 7.6–7.4 (m, 1H, arom), 6.9–6.7 (m, 2H, arom), 5.89 (dq, J$_d$=1.7, J$_q$=7.3, 1H, MeCH), 5.55 (d, J=1.6, 1H, OH), 5.14 (d, J=14.2, 1H, CH(H)), 3.99 (d, J=14.2, 1H, CH(H)), 1.29 (d, J=7.3, 3H, CHMe); GC/MS 224 (Tr—CH$_2$COHAr, C$_{10}$H$_8$F$_2$N$_3$O), 210 (N-ethylheterocycle, C$_{10}$H$_8$F$_2$N$_2$O); [α]$_D$=−4.2° (c 0.4, CHCl$_3$). Analysis calculated for $C_{20}H_{15}F_4N_5O_2$: C 55.43; H 3.49; N 16.16. Found: C 55.41; H 3.57; N 16.00.

EXAMPLE 16

(1R,2R)-3-[2-(2,4-Difluorophenyl)-2-hydroxy-1-methyl-3-(1H-1,2,4-triazol-1-yl)propyl]-7-trifluoromethylquinazolin-4(3H)-one Following a similar procedure to that described in example 1 but using 4-trifluoromethylanthranilic acid (obtained according to U.S. Pat. No. 4,307,113) and recrystallizing the final product from acetonitrile the title compound was obtained as a white solid: mp 142°–143° C.; $^1$H NMR (300 MHz, CDCl$_3$) δ (TMS) 8.65 (s, 1H, N=CH—N), 8.46 (d, J=8.3, 1H, arom), 8.04 (s, 1H, arom), 7.76 (s, 1H, triazole), 7.74 (d, J=8.6, 1H, arom), 7.73 (s, 1H, triazole), 7.48 (q, J=8.5, 1H, arom), 6.9–6.7 (m, 2H, arom), 5.94 (dq, $J_d$=1.5, 1q=7.3, 1H, MeCH), 5.57 (d, J=1.5, 1H, OH), 5.15 (d, J=14.1, 1H, CH(H)), 4.00 (d, J=14.2, 1H, CH(H)), 1.31 (d, J=7.3, 3H, CHMe); $[\alpha]_D$=+4.2° (c 1, CHCl$_3$). Analysis calculated for $C_{21}H_{16}F_5N_5O_2$: C 54.20; H 3.47; N 15.05. Found: C 54.38; H 3.82; N 14.96.

EXAMPLE 17

(1R,2R)-3-[2-(2,4-Difluorophenyl)-2-hydroxy-1-methyl-3-(1H-1,2,4-triazol-1-yl)propyl]-7-(2,2,3,3-tetrafluoropropoxy)quinazolin-4(3H)-one A solution of 2,2,3,3-tetrafluoropropanol (381 mg, 2.9 mmol) in anhydrous NMP (10 mL) was treated with NaH (55% in hexane, 126 mg, 2.9 mmol) for 10 min at room temperature. Once H$_2$ ceased to evolve, (1R,2R)-3-[2-(2,4-difluorophenyl)-2-hydroxy-1-methyl-3-(1H-1,2,4triazol-1-yl)propyl]-7-fluoroquinazolin-4(3H)-one (400 mg, 0.96 mmol, obtained in example 12) was added and the mixture was stirred at 120° C. overnight. Once the reaction was completed, water and EtOAc were added. The aqueous phase was separated and reextracted with further EtOAc. The combined organic extracts were washed with water and brine, dried over anhydrous Na$_2$SO$_4$, filtered, concentrated and purified by flash chromatography to give the title compound as an amorphous white solid (200 mg, 48%): $^1$H NMR (300 MHz, CDCl$_3$) δ (TMS) 8.56 (s, 1H, N=CH—N), 8.29 (d, J=9.5, 1H, arom), 7.76 (s, 1H, triazole), 7.74 (s, 1H, triazole), 7.48 (dt, $J_d$=6.5, $J_t$=8.8, 1H, arom), 7.15 (m, 2H, arom), 6.9–6.7 (m, 2H, arom), 6.08 (tt, J=4.5, J=53, 1H, CHF$_2$), 5.92 (dq, $J_d$=2, $J_q$=7.3, 1H, MeCH), 5.51 (d, J=1.5, 1H, OH), 5.16 (d, J=14.3, 1H, CH(H)), 4.49 (tt, J=1.5, J=12, 2H, CH$_2$), 4.01 (d, J=14.3, 1H, CH(H)), 1.29 (d, J=7.3, 3H, CHMe); GC/MS 304 (N-ethylheterocycle group, $C_{13}H_{12}F_4N_2O_2$), 224 (Tr—CH$_2$COHAr, $C_{10}H_8F_2N_3O$); $[\alpha]_D$=–16.7° (c 1, CHCl$_3$). Analysis calculated for $C_{23}H_{19}F_6N_5O_3$: C 52.38; H 3.63; N 13.28. Found: C 51.84; H 3.68; N 12.29.

EXAMPLE 18

(1R,2R)-3-[2-(2,4-Difluorophenyl)-2-hydroxy-1-methyl-3-(1-H-1,2,4-triazol-1-yl)propyl]-7-(2-fluoroethoxy)quinazolin-4(3N)-one Following the procedure described in example 17 but using 2-fluoroethanol the title compound was obtained as a white solid: mp 191°–194° C.; $^1$H NMR (300 MHz, CDCl$_3$) δ (TMS) 8.54 (s, 1H, N=CH—N), 8.29 (d, J=9.5, 1H, arom), 7.76 (s, 1H, triazole), 7.73 (s, 1H, triazole), 7.48 (dt, $J_d$=6.5, $J_t$=8.8, 1H, arom), 7.3–7.1 (m, 2H, arom), 6.9–6.7 (m, 2H, arom), 5.93 (dq, $J_d$=2, $J_q$=7.3, 1H, MeCH), 5.49 (d, J=1.5, 1H, OH), 5.17 (d, J=14.3, 1H, CH(H)), 4.90 (t, J=4, 1H), 4.75 (t, J=4, 1H), 4.40 (t, J=4, 1H), 4.31 (t, J=4, 1H), 4.02 (d, J=14.3, 1H, CH(H)), 1.29 (d, J=7.3, 3H, CHMe); GC/MS 236 (N-ethylheterocycle, $C_{12}H_{13}FN_2O_2$), 224 (Tr—CH$_2$COHAr, $C_{10}H_8F_2N_3O$); $[\alpha]_D$=–22.9° (c 1, CHCl$_3$). Analysis calculated for $C_{22}H_{20}F_3N_5O_3$: C 57.52; H 4.39; N 15.24. Found: C 57.77; H 4.57; N 14.36.

EXAMPLE 19

(1R,2R)-7-(2,2-Difluoroethoxy)-3-[2-(2,4-difluorophenyl)-2-hydroxy-1-methyl-3-(1H-1,2,4-triazol-1-yl)propyl]quinazolin-4(3H)-one Following the procedure described in example 17 but using 2,2-difluoroethanol the title compound was obtained as a white solid: mp 96°–102° C.; $^1$H NMR (300 MHz, CDCl$_3$) δ (TMS) 8.55 (s, 1H, N=CH—N), 8.27 (d, J=9.5, 1H, arom), 7.76 (s, 1H, triazole), 7.73 (s, 1H, triazole), 7.49 (dt, $J_d$=6.5, $J_t$=8.8, 1H, arom), 7.15 (m, 2H, arom), 6.9–6.7 (m, 2H, arom), 6.16 (tt, J=4, J=55, 1H, CHF$_2$), 5.93 (dq, $J_d$=2, $J_q$=7.3, 1H, MeCH), 5.50 (d, J=1.5, 1H, OH), 5.16 (d, J=14.3, 1H, CH(H)), 4.32 (dt, $J_d$=4, $J_t$=13.2H, OCH$_2$), 4.02 (d, J=14.3, 1H, CH(H)), 1.29 (d, J=7.3, 3H, CHMe); GC/MS 254 (N-ethylheterocycle, $C_{12}H_{12}F_2N_2O_2$), 224 (Tr—CH$_2$COHAr, $C_{10}H_8F_2N_3O$); $[\alpha]_D$=–25.7° (c 1, CHCl$_3$). Analysis calculated for $C_{22}H_{19}F_4N_5O_3$: C 55.35; H 4.01; N 14.67. Found: C 55.25; H 4.35; N 14.29.

EXAMPLE 20

(1R,2R)-3-[2-(2,4-Difluorophenyl)-2-hydroxy-1-methyl-3-(1H-1,2,4-triazol-1-yl)propyl]-7-(2,2,2-trifluoroethoxy)quinazolin-4(3H)-one Following the procedure described in example 17 but using 2,2,2 -trifluoroethanol the title product was obtained as a white amorphous solid: $^1$H NMR (300 MHz, CDCl$_3$) δ (TMS) 8.56 (s, 1H, N=CH—N), 8.29 (d, J=8.8, 1H, arom), 7.76 (s, 1H, triazole), 7.74 (s, 1H, triazole), 7.4–7.1 (m, 3H, arom), 6.9–6.7 (m, 2H, arom), 5.93 (dq, $J_d$=2, $J_q$=7.3, 1H, MeCH), 5.51 (d, J=1.5, 1H, OH), 5.16 (d, J=14.3, 1H, CH(H)), 4.49 (q, J=7.9, 2H, CH$_2$), 4.02 (d, J=14.3, 1H, CH(H)), 1.29 (d, J=7.3, 3H, CHMe); GC/MS 272 (N-ethylheterocycle, $C_{12}H_{11}F_3N_2O_2$), 224 (Tr—CH$_2$COHAr, $C_{10}H_8F_2N_3O$); $[\alpha]_D$=–22.9° (c 1, CHCl$_3$).

EXAMPLE 21

(1R,2R)-3-[2-(2,4-Difluorophenyl)-2-hydroxy-1-methyl-3-(1H-1,2,4-triazol-1-yl)propyl-8-methoxyquinazolin-4(3H)-one Following a similar procedure to that described in example 1 but using 3-methoxyanthranilic acid the title compound was obtained as a white solid: mp 138°–139° C.; $^1$H NMR (80 MHz, CDCl$_3$) δ (TMS) 8.60 (s, 1H, N=CH—N), 7.92 (dd, J=1.3, J=7.7, 1H, arom), 7.74 (s, 1H, triazole), 7.71 (s, 1H, triazole), 7.6–7.3 (m, arom), 7.0–6.6 (m, 2H, arom), 5.95 (dq, $J_d$=1.5, $J_q$=7.3, 1H, MeCH), 5.48 (d, J=1.5, 1H, OH), 5.15 (d, J=14, 1H, CH(H)), 4.05 (s, 3H, OMe), 3.98 (d, J=14, 1H, CH(H)), 1.29 (d, J=7.3, 3H, CHMe); $[\alpha]_D$=–19.7° (c 1, CHCl$_3$). Analysis calculated for $C_{21}H_{19}F_2N_5O_3$: C 59.01; H 4.48; N 16.39. Found: C 58.81; H 4.78; N 16.00.

EXAMPLE 22

(1R,2R)-3-[2-(2,4-Difluorophenyl)-2-hydroxy-1-methyl-3-(1H-1,2,4-triazol-1-yl)propyl]-6,7-dimethoxyquinazolin-4(3H)-one Following a similar procedure to that described in example 1 but using 4,5-dimethoxyanthranilic acid the title compound was obtained as a white solid: mp 157°–159° C.; $^1$H NMR (80 MHz, CDCl$_3$) δ (TMS) 8.70 (s, 1H, N=CH—N), 7.75 (s, 1H, triazole), 7.73 (s, 1H, triazole), 7.66 (s, 1H, arom), 7.6–7.3 (m, 1H, arom), 7.15 (s, 1H, arom), 7.0–6.5 (m, 2H, arom), 5.97 (dq, J$_d$=1.5, J$_q$=7.3, 1H, MeCH), 5.47 (d, J=1.5, 1H, OH), 5.18 (d, J=14, 1H, CH(H)), 4.01 (s, 6H, 2 OMe), 3.98 (d, J=14, 1H, CH(H)), 1.30 (d, J=7.3, 3H, CHMe); [α]$_D$=−11.7° (c 1, CHCl$_3$). Analysis calculated for C$_{22}$H$_{21}$F$_2$N$_5$O$_4$: C 57.77; H 4.63; N 15.31. Found: C 57.83; H 4.86; N 15.21.

EXAMPLE 23

(1R,2R)-3-[2-(2,4-Difluorophenyl)-2-hydroxy-1-methyl-3-(1H-1,2,4-triazol-1-yl)propyl]-8-methyl quinazolin-4(3H)-one Following a similar procedure to that described in example 1 but using 3-methylanthranilic acid the title compound was obtained as a white solid: mp 141°–144° C.; $^1$H NMR (80 MHz, CDCl$_3$) δ (TMS) 8.63 (s, 1H, N=CH—N), 8.20 (dd, J=1.5, J=8, 1H, arom), 7.76 (s, 1H, triazole), 7.72 (s, 1H, triazole), 7.8–7.3 (m, 3H, arom), 7.0–6.5 (m, 2H, arom), 5.95 (dq, J$_d$=1.5, J$_q$=7.3, 1H, MeCH), 5.48 (d, J=1.5, 1H, OH), 5.19 (d, J=14, 1H, CH(H)), 3.98 (d, J=14, 1H, CH(H)), 2.66 (s, 3H, Me), 1.31 (d, J=7.3, 3H, CHMe); [α]$_D$=−49.3° (c 1, CHCl$_3$). Analysis calculated for C$_{21}$H$_{19}$F$_2$N$_5$O$_2$: C 61.31; H 4.66; N 17.02. Found: C 61.72; H 4.83; N 16.87.

EXAMPLE 24

(1R,2R)-3-[2-(2,4-Difluorophenyl)-2-hydroxy-1-methyl-3-(1H-1,2,4-triazol-1-yl)propyl]-6-methylquinazolin-4(3H)-one Following a similar procedure to that described in example 1 but using 5-methylanthranilic acid the title compound was obtained as a white solid: mp 189°–190° C.; $^1$H NMR (80 MHz, CDCl$_3$) δ (TMS) 8.53 (s, 1H, N=CH—N), 8.13 (broad s, 1H, arom), 7.76 (s, 1H, triazole), 7.71 (s, 1H, triazole), 7.8–7.4 (m, 3H, arom), 7.0–6.5 (m, 2H, arom), 5.96 (dq, J$_d$=1.5, J$_q$=7.3, 1H, MeCH), 5.48 (d, J=1.5, 1H, OH), 5.17 (d, J=14, 1H, CH(H)), 3.98 (d, J=14, 1H, CH(H)), 2.51 (s, 3H, Me), 1.30 (d, J=7.3, 3H, CHMe); [α]$_D$=−17.0° (c 1, CHCl$_3$). Analysis calculated for C$_{21}$H$_{19}$F$_2$N$_5$O$_2$: C 61.31; H 4.66; N 17.02. Found: C 61.36; H 4.72; N 17.10.

EXAMPLE 25

(1R,2R)-3-[2-(2,4-Difluorophenyl)-2-hydroxy-1-methyl-3-(1-H-1,2,4-triazol-1-yl)propyl]-5-methyl quinazolin-4(3H)-one Following a similar procedure to that described in example 1 but using 6-methylanthranilic acid the title compound was obtained as a white solid: mp 87°–89° C.; $^1$H NMR (300 MHz, CDCl$_3$) δ (TMS) 8.54 (s, 1H, N=CH—N), 7.79 (s, 1H, triazole), 7.75 (s, 1H, triazole), 7.7–7.6 (m, 2H, arom), 7.49 (dt, J$_d$=6.4, J$_t$=8.8, 1H, arom), 7.30 (dt, J$_t$=0.8, J$_d$=6.7, 1H, arom), 6.9–6.8 (m, 2H, arom), 5.94 (dq, J$_d$=1.7, J$_q$=7.3, 1H, MeCH), 5.49 (d, J=1.7, 1H, OH), 5.19 (d, J=14.2, 1H, CH(H)), 4.09 (d, J=14.2, 1H, CH(H)), 2.95 (s, 3H, Me), 1.29 (d, J=7.3, 3H, CHMe); [α]$_D$=+10.9° (c 1, CHCl$_3$). Analysis calculated for C$_{21}$H$_{19}$F$_2$N$_5$O$_2$: C 61.31; H 4.66; N 17.02. Found: C 61.52; H 4.56; N 17.31.

EXAMPLE 26

(1R,2R)-3-[2-(2,4-Difluorophenyl)-2-hydroxy-1-methyl-3-(1N-1,2,4-triazol-1-yl)propyl]-6,8-dimethylquinazolin-4(3H)-one Following a similar procedure to that described in example 1 but using 3,5-dimethylanthranilic acid the title compound was obtained as a white solid: mp 103°–105° C.; $^1$H NMR (300 MHz, CDCl$_3$) δ (TMS): 8.58 (s, 1H, N=CH—N), 7.98 (s, 1H, arom), 7.75 (s, 1H, triazole), 7.73 (s, 1H, triazole), 7.49 (dt, J$_d$=6.4, J$_t$=8.8, 1H, arom), 7.48 (s, 1H, arom), 6.9–6.8 (m, 2H, arom), 5.94 (dq, J$_d$=1.7, J$_q$=7.3, 1H, MeCH), 5.44 (d, J=1.6, 1H, OH), 5.18 (d, J=14.2, 1H, CH(H)), 4.00 (d, J=14.2, 1H, CH(H)), 2.62 (s, 3H, Me), 2.47 (s, 3H, Me), 1.29 (d, J=7.3, 3H, CHMe); [α]$_D$=−11.1° (c 1, CHCl$_3$). Analysis calculated for C$_{22}$H$_{21}$F$_2$N$_5$O$_2$: C 62.11; H 4.98; N 16.46. Found: C 62.10; H 4.97; N 16.06.

EXAMPLE 27

(1R,2R)-8-Bromo-3-[2-(2,4-difluorophenyl)-2-hydroxy-1-methyl-3-(1H-1,2,4-triazol-1-yl)propyl]-6methylquinazolin4(3H)-one Following a similar procedure to that described in example 1 but using 3-bromo-5-methylanthranilic acid the title compound was obtained as a white solid: mp 116°–123° C.; $^1$H NMR (300 MHz, CDCl$_3$) δ (TMS) 8.71 (s, 1H, N=CH—N), 8.11 (q, J=0.85, 1H, arom), 7.93 (d, J=1.88, 1H, arom), 7.77 (s, 1H, triazole), 7.75 (s, 1H, triazole), 7.50 (dt, J$_d$=6.4, J$_t$=8.8, 1H, arom), 6.9–6.7 (m, 2H, arom), 5.92 (dq, J$_d$=1.7, J$_q$=7.3, 1H, MeCH), 5.53 (d, J=1.7, 1H, OH), 5.15 (d, J=14.2, 1H, CH(H)), 4.00 (d, J=14.2, 1H, CH(H)), 2.51 (s, 3H, Me), 1.31 (d, J=7.3, 3H, CHMe); [α]$_D$=−20.6° (c 1, CHCl$_3$). Analysis calculated for C$_{21}$H$_{18}$BrF$_2$N$_5$O$_2$: C 51.44; H 3.70; N 14.28. Found: C 51.17; H 3.68; N 14.81.

EXAMPLE 28

(1R,2R)-3-[2-(2,4-Difluorophenyl)-2-hydroxy-1-methyl-3-(1H-1,2,4-triazol-1-yl)propyl]pyrido[2,3-d]pyrimidin-4(3H)-one Following a similar procedure to that described in example 1 but using 2-aminonicotinic acid the title compound was obtained as a white solid: mp 210°–211° C.; $^1$H NMR (80 MHz, CDCl$_3$) δ (TMS) 9.03 (dd, J=2, J=4.5, 1H, arom), 8.81 (s, 1H, N=CH—N), 8.67 (dd, J=2, J=8.7, 1H, arom), 7.77 (s, 1H, triazole), 7.73 (s, 1H, triazole), 7.6–7.3 (m, 2H, arom), 6.9–6.7 (m, 2H, arom), 5.90 (dq, J$_d$=1.6, J$_q$=7, 1H, MeCH), 5.61 (d, J=1.6, 1H, OH), 5.14 (d, J=14, 1H, CH(H)), 4.05 (d, J=14, 1H, CH(H)), 1.32 (d, J=7, 3H, CHMe); [α]$_D$=+0.8° (c 1, CHCl$_3$). Analysis calculated for C$_{19}$H$_{16}$F$_2$N$_6$O$_2$: C 57.29; H 4.05; N 21.10. Found: C 57.27; H 3.81; N 20.71.

EXAMPLE 29

(1R,2R)-7-[(4-Chlorophenyl)sulfonyl]-3-[2-(2,4-difluorophenyl)-2-hydroxy-1-methyl-3-(1H-1,2,4-triazol-1-yl)propyl thieno[3,2-d]pyrimidin-4(3H)-one Following a similar procedure to that described in example 1 but using 3-amino-4-[(4-chlorophenyl)sulfonyl]thiophene-2-carboxylic acid, the title compound was obtained as an amorphous solid in a similar yield: $^1$H NMR (80 MHz, CDCl$_3$) δ (TMS) 8.68 (s, 2H, SCH=, N=CH—N), 8.19 (d, J=8.6, 2H, arom), 7.73 (s, 1H, triazole), 7.70 (s, 1H, triazole), 7.52 (d, J=8.6, 2H, arom), 7.6–7.3 (m, 1H, arom), 6.9–6.7 (m, 2H, arom), 5.88 (dq, J$_d$=1.6, J$_q$=7, 1H, MeCH), 5.57 (d, J=1.6, 1H, OH), 5.09 (d, J=14, 1H, CH(H)), 3.94 (d, J=14, 1H, CH(H)), 1.27 (d, J=7, 3H, CHMe); [α]$_D$=−31.7° (c 1, CHCl$_3$). Analysis calculated for C$_{24}$H$_{18}$ClF$_2$N$_5$O$_4$S$_2$: C 49.87; H 3.14; N 12.12; S 11.09. Found: C 49.80; H 3.30; N 11.96; S 10.72.

EXAMPLE 30

(1R,2R)-3-[2-(2,4-Difluorophenyl)-2-hydroxy-1-methyl-3-(1H-1,2,4-triazol-1-yl)propyl]-7-(propylsulfonyl)thieno[3,2-d]pyrimidin-4(3H)-one Following a similar procedure to that described in example 1 but using 3-amino-4-(propylsulfonyl)thiophene-2-carboxylic acid, the title compound was obtained as a white solid: mp 115°–122° C.; $^1$H NMR (80 MHz, CDCl$_3$) δ (TMS) 8.75 (s, 1H, arom), 8.61 (s, 1H, arom), 7.77 (s, 1H, triazole), 7.75 (s, 1H, triazole), 7.48 (q, J=8, 1H, arom), 7.0–6.7 (m, 2H, arom), 5.95 (dq, J$_d$=1.6, J$_q$=7, 1H, MeCH), 5.61 (d, J=1.6, 1H, OH), 5.15 (d, J=14, 1H, CH(H)), 4.00 (d, J=14, 1H, CH(H)), 3.57 (d, J=8, 1H, SO$_2$CH(H)), 3.48 (d, J=8, 1H, SO$_2$CH(H)), 2.1–1.6 (m, 2H, SO$_2$CH$_2$CH$_2$), 1.32 (d, J=7, 3H, CHMe), 1.08 (t, J=7.5, 3H, SO$_2$CH$_2$CH$_2$CH$_3$); [α]$_D$=−15.8° (c 1, CHCl$_3$). Analysis calculated for C$_{21}$H$_{21}$F$_2$N$_5$O$_4$S$_2$: C 49.51; H 4.15; N 12.56; S 12.58. Found: C 48.67; H 4.24; N 12.71; S 12.26.

EXAMPLE 31

(1R,2R)-6-(4-Chlorophenyl)-3-[2-(2,4-difluorophenyl)-2-hydroxy-1-methyl-3-(1H-1,2,4-triazol-1-yl)propyl]thieno[3,2-d]pyrimidin-4(3H)-one Following a similar procedure to that described in example 1 but using 3-amino-5-(4-chlorophenyl)thiophene-2-carboxylic acid (obtained as described in Hartmann, *Synthesis* 1984, 275) and recrystallizing the final product from acetonitrile the title compound was obtained as a white solid: mp 158°–160° C.; $^1$H NMR (300 MHz, CDCl$_3$) δ (TMS) 8.60 (s, 1H, N=CH—N), 7.78 (s, 1H, triazole), 7.74 (s, 1H, triazole), 7.66 (d, J=6.6, 2H, arom), 7.51 (s, 1H, thiophene), 7.50 (dt, J$_d$=6.4, J$_t$=8.8, 1H, arom), 7.44 (d, J=6.6, 2H, arom), 6.9–6.7 (m, 2H, arom), 5.98 (dq, J$_d$=1.6, J$_q$=7.3, 1H, MeCH), 5.54 (d, J=1.6, 1H, OH), 5.19 (d, J=14.2, 1H, CH(H)), 4.02 (d, J=14.2, 1H, CH(H)), 1.31 (d, J=7.3, 3H, CHMe); [α]$_D$=+14.0° (c 1, CHCl$_3$). Analysis calculated for C$_{24}$H$_{18}$ClF$_2$N$_5$O$_2$S: C 56.09; H 3.53; N 13.63; S 6.24. Found: C 55.78; H 3.59; N 13.53; S 5.92.

EXAMPLE 32

(1R,2R)-4-[3-[2-(2,4-Difluorophenyl)-2-hydroxy-1-methyl-3-(1H-1,2,4-triazol-1-yl)propyl]-4-oxo-3,4-dihydrothieno[3,2-d]pyrimidin-6-yl]benzonitrile Following a similar procedure to that described in example 1 but using 3-amino-5-(4-cyanophenyl)thiophene-2-carboxylic acid the title compound was obtained as a white solid: mp 231°–232° C.; $^1$H NMR (300 MHz, CDCl$_3$) δ (TMS) 8.62 (s, 1H, N=CH—N), 7.83 (dt, J$_d$=2, J$_t$=8.6, 2H, arom), 7.78 (s, 2H, triazole), 7.73 (dt, J$_d$=2, J$_t$=8.6, 2H, arom), 7.64 (s, 1H, thiophene), 7.49 (dt, J$_d$=6.4, J$_t$=8.8, 1H, arom), 6.9–6.7 (m, 2H, arom), 5.98 (dq, J$_d$=1.6, J$_q$=7.3, 1H, MeCH), 5.57 (d, J=1.6, 1H, OH), 5.18 (d, J=14.2, 1H, CH(H)), 4.02 (d, J=14.2, 1H, CH(H)), 1.32 (d, J=7.3, 3H, CHMe); [α]$_D$=+15.2° (c 0.76, CHCl$_3$). Analysis calculated for C$_{25}$H$_{18}$F$_2$N$_6$O$_2$S: C 59.52; H 3.60; N 16.68; S 6.35. Found: C 58.29; H 3.55; N 15.68; S 5.86.

EXAMPLE 33

(1R,2R)-3-[2-(2,4-Difluorophenyl)-2-hydroxy-1-methyl-3-(1H-1,2,4-triazol-1-yl)propyl]-6-[(4-trifluoromethyl)phenyl]thieno[3,2-d]pyrimidin-4(3H)-one Following a similar procedure to that described in example 1 but using 3-amino-5-(4-trifluoromethylphenyl) thiophene-2-carboxylic acid the title compound was obtained as a white amorphous solid: $^1$H NMR (300 MHz, CDCl$_3$) δ (TMS) 8.61 (s, 1H, N=CH—N), 8.08 (d, J=8.1, 2H, arom), 7.77 (s, 1H, triazole), 7.74 (s, 1H, triazole), 7.72 (d, J=8.1, 2H, arom), 7.50 (m, 2H, thiophene, arom), 6.9–6.7 (m, 2H, arom), 5.97 (dq, J$_d$=1.5, J$_q$=7.3, 1H, MeCH), 5.50 (d, J=1.5, 1H, OH), 5.20 (d, J=14.2, 1H, CH(H)), 3.99 (d, J=14.2, 1H, CH(H)), 1.30 (d, J=7.3, 3H, CHMe); [α]$_D$=+12.3° (c 1, CHCl$_3$). Analysis calculated for C$_{25}$H$_{18}$F$_5$N$_5$O$_2$S: C 54.84; H 3.31; N 12.79; S 5.86. Found: C 54.89; H 3.43; N 12.46; S 5.41.

EXAMPLE 34

(1R,2R)-3-[2-(2,4-Difluorophenyl)-2-hydroxy-1-methyl-3-(1H-1,2,4-triazol-1-yl)propyl]-6-[4-(2,2,3,3-tetrafluoropropoxy)phenyl]thieno[3,2-d]pyrimidin-4(3H)-one Following a similar procedure to that described in example 1 but using 3-amino-5-[4-(2,2,3,3-tetrafluoropropoxy)phenyl]thiophene-2-carboxylic acid the title compound was obtained as a white amorphous solid: $^1$H NMR (80 MHz, CDCl$_3$) δ (TMS) 8.60 (s, 1H, N=CH—N), 7.95 (dt, J$_t$=2, J$_d$=9, 2H, arom), 7.78 (s, 2H, triazole), 7.50 (s, 1H, thiophene), 7.38 (dt, J$_d$=6.5, J$_t$=8.8, 1H, arom), 7.02 (dt, J$_t$=2, J$_d$=9, 2H, arom), 6.9–6.7 (m, 2H, arom), 6.06 (tt, J=53, J=4.5, 1H, CHF$_2$), 5.97 (dq, J$_d$=1.5, J$_q$=7.3, 1H, MeCH), 5.55 (d, J=1.6, 1H, OH), 5.18 (d, J=14.2, 1H, CH(H)), 4.41 (tt, J=12, J=1.5, 2H, CH$_2$), 4.02 (d, J=14.2, 1H, CH(H)), 1.32 (d, J=7.3, 3H, CHMe); [α]$_D$=+11.7° (c 0.76, CHCl$_3$). Analysis calculated for C$_{27}$H$_{21}$F$_6$N$_5$O$_3$S: C 53.20; H 3.47; N 11.49; S 5.26. Found: C 53.61; H 3.39; N 10.96; S 4.60.

EXAMPLE 35

(1R,2R)-5-[2-(2,4-Difluorophenyl)-2-hydroxy-1-methyl-3-(1H-1,2,4-triazol-1-yl)propyl]-1-(4-fluorophenyl)-1,5dihydropyrazolo[3,4-d]pyrimidin-4-one Following a similar procedure to that described in example 1 but using 5-amino-1-(4-fluorophenyl)-1H-pyrazole-4-carboxylic acid the title compound was obtained as a white solid: mp 217°–218° C.; $^1$H NMR (80 MHz, CDCl$_3$) δ (TMS) 8.57 (s, 1H, N=CH—N), 8.26 (s, 1H, pyrazole), 8.2–7.8 (m, 2H, arom), 7.76 (s, 1H, triazole), 7.73 (s, 1H, triazole), 7.49 (dt, J$_d$=6.5, J$_t$=9, 1H, arom), 7.4–7.2 (m, 2H, arom), 6.9–6.7 (m, 2H, arom), 5.97 (dq, J$_d$=1.5, J$_q$=7.3, 1H, MeCH), 5.54 (d, J=1.5, 1H, OH), 5.17 (d, J=14.2, 1H, CH(H)), 3.96 (d, J=14.2, 1H, CH(H)), 1.28 (d, J=7.3, 3H, CHMe); [α]$_D$=−61.9° (c 1, CHCl$_3$). Analysis calculated for C$_{23}$H$_{18}$F$_3$N$_7$O$_2$: C 57.38; H 3.77; N 20.37. Found: C 57.41; H 3.68; N 20.19.

EXAMPLE 36

(1R,2R)-1-(4-Chlorophenyl)-5-[2-(2,4-difluorophenyl)-2-hydroxy-1-methyl-3-(1H-1,2,4-triazol-1-yl)propyl]-1,5dihydropyrazolo[3,4-d]pyrimidin-4-one Following a similar procedure to that described in example 1 but using 5-amino-1-(4-chlorophenyl)-1H-pyrazole-4-carboxylic acid the title compound was obtained as a white solid: mp 237°–238° C.; $^1$H NMR (80 MHz, CDCl$_3$) δ (TMS) 8.58 (s, 1H, N=CH—N), 8.27 (s, 1H, pyrazole), 8.10 (d, J=8.8, 2H, arom), 7.76 (s, 1H, triazole), 7.73 (s, 1H, triazole), 7.49 (dt, $J_d$=6.5, $J_t$=9, 1H, arom), 7.48 (d, J=8.8, 2H, arom), 6.9–6.7 (m, 2H, arom), 5.97 (dq, $J_d$=1.5, $J_q$=7.3, 1H, MeCH), 5.54 (d, J=1.5, 1H, OH), 5.16 (d, J=14.2, 1H, CH(H)), 3.96 (d, J=14.2, 1H, CH(H)), 1.29 (d, J=7.3, 3H, CHMe); $[\alpha]_D$=−68.3° (c 1, CHCl$_3$). Analysis calculated for $C_{23}H_{18}ClF_2N_7O_2$: C 55.48; H 3.64; N 19.69. Found: C 55.10; H 3.89; N 19.30.

EXAMPLE 37

(1R,2R)-S[2-(2,4-Difluorophenyl)-2-hydroxy-1-methyl-3-(1H-1,2,4-triazol-1-yl)propyl]-1-[4-(trifluoromethyl)phenyl]-1,5-dihydropyrazolo[3,4-d]pyrimidin-4-one Following a similar procedure to that described in example 1 but using 5-amino-1-(4-trifluoromethylphenyl)-1H-pyrazole-4-carboxylic acid the title compound was obtained as a white solid: mp 212°–213° C.; $^1$H NMR (80 MHz, CDCl$_3$) δ (TMS) 8.61 (s, 1H, N=CH—N), 8.36 (d, J=8.7, 2H, arom), 8.31 (s, 1H, pyrazole), 7.79 (d, J=8.7, 2H, arom), 7.76 (s, 1H, triazole), 7.73 (s, 1H, triazole), 7.48 (dt, $J_d$=6.5, $J_t$=9, 1H, arom), 6.9–6.7 (m, 2H, arom), 5.97 (dq, $J_d$=1.5, $J_q$=7.3, 1H, MeCH), 5.58 (d, J=1.5, 1H, OH), 5.17 (d, J=14.2, 1H, CH(H)), 3.96 (d, J=14.2, 1H, CH(H)), 1.30 (d, J=7.3, 3H, CHMe); $[\alpha]_D$=+2.3° (c 1, CHCl$_3$). Analysis calculated for $C_{24}H_{18}F_5N_7O_2$: C 54.24; H 3.41; N 18.45. Found: C 53.88; H 3.91; N 18.24.

EXAMPLE 38

(1R,2R)-3-[2-(2,4-Difluorophenyl)-2-hydroxy-1-methyl-3-(1H-1,2,4-triazol-1-yl)propyl]benzo[g]quinazolin4(3H)-one Following a similar procedure to that described in example 1 but using 3-amino-2-naphtoic acid the title compound was obtained as a slightly yellowish solid: mp 200°–102° C.; $^1$H NMR (300 MHz, CDCl$_3$) δ (TMS) 8.95 (s, 1H, arom), 8.57 (s, 1H, N=CH—N), 8.24 (s, 1H, arom), 8.2–7.9 (m, 2H, arom), 7.77 (s, 1H, triazole), 7.72 (s, 1H, triazole), 7.7–7.3 (m, 3H, arom), 6.9–6.8 (m, 2H, arom), 5.98 (dq, $J_d$=1.2, $J_q$=7.3, 1H, MeCH), 5.51 (d, J=1.6, 1H, OH), 5.21 (d, J=14.1, 1H, CH(H)), 4.08 (d, J=14.1, 1H, CH(H)), 1.32 (d, J=7.3, 3H, CHMe); $[\alpha]_D$=+3.6° (c 1, CHCl$_3$). Analysis calculated for $C_{24}H_{19}F_2N_5O_2$: C 64.42; H 4.28; N 15.65. Found: C 64.14; H 4.46; N 15.13.

EXAMPLE 39

(1R,2R)-7-(4-Chlorophenoxy)-3-[2-(2,4-difluorophenyl)-2-hydroxy-1-methyl-3-(1H-1,2,4-triazol-1-yl)propyl]quinazolin-4(3H)-one Following a similar procedure to that described in example 17 but using 4-chlorophenol, the title product was obtained as a white solid: mp 198°–199° C.; $^1$H NMR (300 MHz, CDCl$_3$) δ (TMS) 8.50 (s, 1H, N=CH—N), 8.26 (d, J=8.7, 1H, arom), 7.75 (s, 1H, triazole), 7.68 (s, 1H, triazole), 7.47 (dt, $J_d$=6.5, $J_t$=9, 1H, arom), 7.34 (d, J=8.6, 2H, arom), 7.15 (dd, J=2.4, J=8.6, 1H, arom), 7.13 (d, J=2.2, 1H, arom), 7.03 (d, J=8.6, 2H, arom), 6.9–6.7 (m, 2H, arom), 5.97 (dq, $J_d$=1.5, $J_q$=7.3, 1H, MeCH), 5.58 (d, J=1.5, 1H, OH), 5.17 (d, J=14.2, 1H, CH(H)), 3.96 (d, J=14.2, 1H, CH(H)), 1.30 (d, J=7.3, 3H, CHMe); GC/MS 300 and 302 (N-ethylheterocycle, $C_{16}H_{13}ClN_2O_2$), 224 (TrCH$_2$COHAr, $C_{10}H_8F_2N_3O$); $[\alpha]_D$=−22° (c 0.1, CHCl$_3$). Analysis calculated for $C_{26}H_{20}ClF_2N_5O_3$: C 59.61; H 3.85; N 13.37. Found: C 59.72; H 3.57; N 12.96.

EXAMPLE 40

(1R,2R)-7-[4-(4-Chlorophenyl)-1-piperazinyl]-3-[2-(2,4-difluorophenyl)-2-hydroxy--methyl-3-(1H-1,2,4-triazol-1-yl)propyl]quinazolin-4(3H)-one To a solution of 4-(4-chlorophenyl)piperazine (760 mg, 3.8 mmol) in anhydrous NMP (10 mL) was added (1R,2R)-3-[2-(2,4-difluorophenyl)-2-hydroxy-1-methyl-3-(1H-1,2,4-triazol-1-yl)propyl]-7-fluoroquinazolin-4(3H)-one (400 mg, 0.96 mmol, obtained in example 12). The mixture was stirred at 130° C. overnight. Following then the procedure described in example 17 the title compound was obtained as a white solid: mp 218°–219° C.; $^1$H NMR (300 MHz, CDCl$_3$) δ (TMS) 8.49 (s, 1H, N=CH—N), 8.19 (d, J=8.9, 1H, arom), 7.76 (s, 1H, triazole), 7.73 (s, 1H, triazole), 7.47 (dt, $J_d$=6.5, $J_t$=9, 1H, arom), 7.24 (dt, $J_t$=2.8, $J_d$=9.6, 2H, arom), 7.14 (dd, J=2.4, J=9.0, 1H, arom), 7.06 (d, J=2.3, 1H, arom), 6.89 (dt, $J_t$=2.8, $J_d$=9.6, 2H, arom), 6.9–6.7 (m, 2H, arom), 5.91 (dq, $J_d$=1.5, $J_q$=7.3, 1H, MeCH), 5.46 (d, J=1.5, 1H, OH), 5.17 (d, J=14.2, 1H, CH(H)), 4.03 (d, J=14.2, 1H, CH(H)), 3.6–3.5 (m, 4H, piperazine), 3.4–3.3 (m, 4H, piperazine), 1.28 (d, J=7.3, 3H, CHMe); MS (DIP) 367 (N-ethylheterocycle, $C_{20}H_{20}ClN_4O$), 224 (Tr—CH$_2$COHAr, $C_{10}H_8F_2N_3O$); $[\alpha]_D$=−34.1° (c 0.1, CHCl$_3$). Analysis calculated for $C_{30}H_{28}ClF_2N_7O_2$: C 60.86; H 4.77; N 16.56. Found: C 60.65; H 4.97; N 15.94.

EXAMPLE 41

(1R,2R)-7-[4-(4-Chlorophenyl)-1-piperazinyl]-3-[2-(2,4-difluorophenyl)-2-hydroxy-1-methyl-3-(1H-1,2,4-triazol-1-yl)propyl]-6-fluoroquinazolin-4(3H)-one Following the procedure described in the preceding example but using (1R,2R)-6,7-difluoro-3-[2-(2,4-difluorophenyl)-2-hydroxy-1-methyl-3-(1 H-1,2,4 -triazol-1-yl)propyl]quinazolin-4(3H)-one (prepared in example 15) the title compound was obtained as a white solid: mp 130°–133° C.; $^1$H NMR (300 MHz, CDCl$_3$) δ (TMS) 8.50 (s, 1H, N=CH—N), 7.90 (d, J=12.8, 1H, arom), 7.76 (s, 1H, triazole), 7.74 (s, 1H, triazole), 7.48 (dt, $J_d$=6.5, $J_t$=9, 1H, arom), 7.24 (dt, $J_t$=2.8, $J_d$=9.6, 2H, arom), 7.21 (d, J=9.0, 1H, arom), 6.90 (dt, $J_t$=2.8, $J_d$=9.6, 2H, arom), 6.9–6.7 (m, 2H, arom), 5.91 (dq, $J_d$=1.5, $J_q$=7.3, 1H, MeCH), 5.48 (d, J=1.5, 1H, OH), 5.16 (d, J=14.2, 1H, CH(H)), 4.01 (d, J=14.2, 1H, CH(H)), 3.44 (m, 4H, piperazine), 3.35 (m, 4H, piperazine), 1.28 (d, J=7.3, 3H, CHMe); MS (DIP) 386 (N-ethylheterocycle, $C_{20}H_{20}ClFN_4O$), 224 (Tr—CH$_2$COHAr, $C_{10}H_8F_2N_3O$); $[\alpha]_D$=+33.8° (c 0.5, CHCl$_3$). Analysis calculated for $C_{30}H_{27}ClF_3N_7O_2$: C 59.10; H 4.47; N 16.09. Found: C 58.86; H 4.65; N 16.01.

EXAMPLE 42

(1R,2R)-3-[2-(2,4-Difluorophenyl)-2-hydroxy-1-methyl-3-(1H-1,2,4-triazol-1-yl)propyl]-7-[4-(4-nitrophenyl)-1-piperazinyl]quinazolin-4(3H)-one Following a similar procedure to that described in example 40 but using 4-(4-nitrophenyl)piperazine the title compound was obtained as an orange-coloured solid: mp 287°–289° C.; $^1$H NMR (300 MHz, CDCl$_3$) δ (TMS) 8.50 (s, 1H, N=CH—N), 8.3–8.1 (m, 3H, arom), 7.76 (s, 1H, triazole), 7.73 (s, 1H, triazole), 7.47 (dt, $J_d$=6.5, $J_t$=9, 1H, arom), 7.10 (dd, J=2.3, J=9.0, 1H, arom), 7.03 (d, J=2.3, 1H, arom), 6.9–6.7 (m, 4H, arom), 5.92 (dq, $J_d$=1.5, $J_q$=7.3, 1H, MeCH), 5.46 (d, J=1.5, 1H, OH), 5.17 (d, J=14.2, 1H, CH(H)), 4.03 (d, J=14.2, 1H, CH(H)), 3.67 (s, 8H, piperazine), 1.28 (d, J=7.3, 3H, CHMe); [α]$_D$=−41° (c 0.2, CHCl$_3$). Analysis calculated for C$_{30}$H$_{28}$F$_2$N$_8$O$_4$: C 59.80; H 4.68; N 18.59. Found: C 60.03; H 4.42; N 18.31.

EXAMPLE 43

(1R,2R)-7-[4-(4-Aminophenyl)-1-piperazinyl]-3-[2-(2,4-difluorophenyl)-2-hydroxy-1-methyl-3-(1H-1,2,4-triazol-1-yl)propyl]quinazolin-4(3H)-one A solution of the product obtained in example 42 (1.3 g, 2.1 mmol) in EtOH (200 mL) and CHCl$_3$ (5 mL) was treated with Pd/C (5%, 1 g) and H$_2$ at 1 atm for 24 h. The catalyst was filtered off and the resulting solution was evaporated to dryness to give the title compound as a slightly greenish solid (1.2 g, 100%): mp 170°–173° C.; $^1$H NMR (300 MHz, MeOH-d$_4$) δ (MeOH) 8.57 (s, 1H, N=CH—N), 8.2–8.0 (m, 2H, arom, triazole), 7.90 (s, 1H, triazole), 7.39 (dt, J$_d$=6.5, J$_t$=9, 1H, arom), 7.4–7.0 (m, arom), 7.29 (dt, J$_t$=2.2, J$_d$=9.3, 1H, arom), 7.15 (ddd, J=2.4, J=8.7, J=11.5, 1H, arom), 6.89 (dt, Id=2.5, J$_t$=8.5, 1H, arom), 6.05 (q, J$_q$=7.3, 1H, MeCH), 5.06 (d, J=14.2, 1H, CH(H)), 4.18 (d, J=14.2, 1H, CH(H)), 3.7–3.5 (m, 4H, piperazine), 3.5–3.3 (m, 4H, piperazine), 1.29 (d, J=7.3, 3H, CHMe).

EXAMPLE 44

(1R,2R)-3-[2-(2,4-Difluorophenyl)-2-hydroxy-1-methyl-3-(1H-1,2,4-triazol-1-yl)propyl]-7-[4-[4-(2,4-dihydro-3H-1,2,4-triazol-3-one-4-yl)phenyl]-1-piperazinyl]quinazolin-4(3H)-one (a) A solution of the product obtained in example 43 (1.2 g, 2.1 mmol) in pyridine (75 mL) was treated with phenyl chloroformate (393 mg, 2.5 mmol) at room temperature for 3 h. The reaction was quenched by the addition of 10% aqueous NaHCO$_3$ solution. Next, most of the pyridine was removed in vacuo and the residue was partitioned between CHCl$_3$ and H$_2$O. The layers were separated and the organic phase was dried over Na$_2$SO$_4$, filtered, concentrated and purified by flash chromatography to give the corresponding phenyl carbamate as a yellowish solid (1.2 g, 83%): mp 137°–143° C.; $^1$H NMR (300 MHz, CDCl$_3$) δ (CDCl$_3$) 8.49 (s, 1H, N=CH—N), 8.19 (d, J=8.9, 1H, arom), 7.76 (s, 1H, triazole), 7.73 (s, 1H, triazole), 7.47 (dt, J$_d$=6.5, J$_t$=9, 1H, arom), 7.4–6.5 (m, arom), 5.92 (q, J$_q$=7.3, 1H, MeCH), 5.45 (d, J=1.5, 1H, OH), 5.17 (d, J=14.2, 1H, CH(H)), 4.03 (d, J=14.2, 1H, CH(H)), 3.6–3.5 (m, 4H, piperazine), 3.4–3.3 (m, 4H, piperazine), 1.28 (d, J=7.3, 3H, CHMe); [α]$_D$=+6.0° (c 0.2, MeOH).

(b) The above product (1.2 g, 1.7 mmol) was dissolved in 1,2-dimethoxyethane (25 mL) and was treated with hydrazine hydrate (693 mg, 14 mmol) at 80° C. for 3 h. Solvents were removed in vacuo and the resulting yellowish residue was recrystallized from MeOH—H$_2$O to give the corresponding semicarbazide as an off-white solid (900 mg, 84%): mp 190°–193° C.; $^1$H NMR (300 MHz, MeOH-d$_4$) δ (MeOH) 8.45 (s, 1H, N=CH—N), 8.17 (s, 1H, triazole), 8.12 (d, J=9.0, 1H, arom), 7.64 (s, 1H, triazole), 7.5–7.2 (m, arom), 7.2–6.7 (m, arom), 6.04 (q, J$_q$=7.3, 1H, MeCH), 5.07 (d, J=14.2, 1H, CH(H)), 4.13 (d, J=14.2, 1H, CH(H)), 3.6–3.5 (m, 4H, piperazine), 3.4–3.3 (m, 4H, piperazine), 1.27 (d, J=7.3, 3H, CHMe); [α]$_{D=+5.2°}$ (c 0.2, MeOH).

(c) The product obtained in section (b) (900 mg) was dissolved in DMF (10 mL) and treated with formamidine acetate (665 mg, 6.3 mmol) at 80° C. for 3 h. The product was isolated in a similar manner to that described in section (b) and finally was flash chromatographed to give the title product as an off-white solid: $^1$H NMR (300 MHz, CDCl$_3$) δ (TMS) 10.4 (broad s, 1H, NH), 8.50 (s, 1H, N=CH—N), 8.19 (d, J=8.9, 1H, arom), 7.77 (s, 1H, triazole), 7.72 (s, 1H, triazole), 7.63 (s, 1H, triazolone), 7.44 (d, J=9, 2H, arom), 7.5–7.4 (m, 1H, arom), 7.14 (dd, J=2.3, J=9.0, 1H, arom), 7.07 (d, J=2.3, 1H, arom), 7.00 (d, J=9, 2H, arom), 6.9–6.7 (m, 2H, arom), 5.90 (q, J=7.3, 1H, MeCH), 5.46 (broad s, 1H, OH), 5.18 (d, J=14.2, 1H, CH(H)), 4.03 (d, J=14.2, 1H, CH(H)), 3.60 (m, 4H, piperazine), 3.40 (m, 4H, piperazine), 1.27 (d, J=7.3, 3H, CHMe).

EXAMPLE 45

(1R,2R)-3-[2-(2,4-Difluorophenyl)-2-hydroxy-1-methyl-3-(1H-1,2,4-triazol-1-yl)propyl]-7-[4-[4-[2,4-dihydro-2-(3-pentyl)-3H-1,2,4-triazol-3-one-4-yl]phenyl]-1-piperazinyl]quinazolin-4(3H)-one A solution of the product obtained in the preceding example (100 mg) in DMF (5 mL) was treated with C$_{22}$CO$_3$ (50 mg, 0.16 mmol) and 3-bromopentane (47 mg, 0.32 mmol) at 65° C. for 18 h. The mixture was partitioned between EtOAc and H$_2$O, the organic phase was separated, dried, concentrated and purified by flash chromatography to give the title compound as a cream-coloured solid (20 mg): mp 208°–210° C.; $^1$H NMR (300 MHz, CDCl$_3$) δ (TMS) 8.49 (s, 1H, N=CH—N), 8.18 (d, J=8.9, 1H, arom), 7.76 (s, 1H, triazole), 7.72 (s, 1H, triazole), 7.64 (s, 1H, triazolone), 7.44 (d, J=9, 2H, arom), 7.5–7.4 (m, 1H, arom), 7.14 (dd, J=2.3, J=9.0, 1H, arom), 7.06 (d, J=2.3, 1H, arom), 7.02 (d, J=9, 2H, arom), 6.9–6.7 (m, 2H, arom), 5.91 (dq, J$_d$=1.5, J$_q$=7.3, 1H, MeCH), 5.46 (d, J=1.5, 1H, OH), 5.17 (d, J=14.2, 1H, CH(H)), 4.1–3.9 (m, 1H, CHEt$_2$), 4.03 (d, J=14.2, 1H, CH(H)), 3.60 (m, 4H, piperazine), 3.39 (m, 4H, piperazine), 1.9–1.6 (m, 4H, CH(CH$_2$CH$_3$)$_2$), 1.27 (d, J=7.3, 3H, CHMe), 0.88 (t, J=7.3, 6H, CH(CH$_2$CH$_3$)$_2$); GC/MS 711 (M+), 486 (N-ethylheterocycle, C$_{27}$H$_{32}$N$_7$O$_2$), 224 (Tr—CH$_2$COHAr, C$_{10}$H$_8$F$_2$N$_3$O); [α]$_D$=−28.5° (c 0.2, CHCl$_3$). Analysis calculated for C$_{37}$H$_{40}$F$_2$N$_{10}$O$_3$: C 62.52; H 5.67; N 19.71. Found: C 61.60; H 5.65; N 19.26.

EXAMPLE 46

(1R,2R)-3-[2-(2,4-Difluorophenyl)-2-hydroxy-1-methyl-3-(1H-1,2,4-triazol-1-yl)propyl]-7-(4-methyl-1-piperazinyl)quinazolin-4(3H)-one Following the procedure described in example 40 but using N-methylpiperazine the title compound was obtained as a white solid: mp 121°–131° C.; $^1$H NMR (300 MHz, CDCl$_3$) δ (TMS) 8.47 (s, 1H, N=CH—N), 8.15 (d, J=9.0, 1H, arom), 7.75 (s, 1H, triazole), 7.72 (s, 1H, triazole), 7.5–7.4 (m, 1H, arom), 7.10 (dd, J=2.4, J=9.0, 1H, arom), 7.02 (d, J=2.3, 1H, arom), 6.9–6.6 (m, 2H, arom), 5.91 (dq, J$_d$=1.6, J$_q$=7.3, 1H, MeCH), 5.44 (d, J=1.6, 1H, OH), 5.17 (d, J=14.2, 1H, CH(H)), 4.02 (d, J=14.2, 1H, CH(H)), 3.45 (m, 4H, piperazine), 2.58 (m, 4H, piperazine), 2.36 (3H, NMe), 1.27 (d, J=7.3, 3H, CHMe); GC/MS 271 and 272 (N-ethylheterocycle, C$_{15}$H$_{20}$N$_4$O), 224 (Tr—CH$_2$COHAr, C$_{10}$H$_8$F$_2$N$_3$O); [α]$_D$=−14.3° (c 1, CHCl$_3$). Analysis calculated for C$_{25}$H$_{27}$F$_2$N$_7$O$_2$.1/2H$_2$O: C 59.57; H 5.56; N 19.44. Found: C 59.63; H 5.76; N 18.46.

EXAMPLE 47

(1R,2R)-3-[2-(2,4-Difluorophenyl)-2-hydroxy-1-methyl-3-(1H-1,2,4-triazol-1-yl)propyl]-6fluoro-7-(4-methyl-1-piperazinyl)quinazolin-4(3H)-one Following the procedure described in example 41, but using N-methylpiperazine the title product was obtained as a white solid: mp 106°–112 ° C.; $^1$H NMR (300 MHz, CDCl$_3$) δ (TMS) 8.49 (s, 1H, N=CH—N), 7.86 (d, J=13, 1H, arom), 7.76 (s, 1H, triazole), 7.73 (s, 1H, triazole), 7.48 (dt, J$_d$=6.5, J$_t$=9, 1H, arom), 7.16 (d, J=7.8, 1H, arom), 6.9–6.7 (m, 2H, arom), 5.91 (dq, J$_d$=1.5, J$_q$=7.3, 1H, MeCH), 5.47 (d, J=1.5, 1H, OH), 5.15 (d, J=14.2, 1H, CH(H)), 3.98 (d, J=14.2, 1H, CH(H)), 3.32 (m, 4H, piperazine), 2.63 (m, 4H, piperazine), 2.37 (s, 3H, NMe), 1.28 (d, J=7.3, 3H, CHMe); GC/MS 289 and 290 (N-ethylheterocycle, C$_{15}$H$_{19}$FN$_4$O), 224 (Tr—CH$_2$COHAr, C$_{10}$H$_8$F$_2$N$_3$O). Analysis calculated for C$_{25}$H$_{26}$F$_3$N$_7$O$_2$.CHCl$_3$: C 49.34; H 4.30; N 15.49. Found: C 50.90; H 4.56; N 15.83.

EXAMPLE 48

(1R,2)-3-[2-(2,4-Difluorophenyl)-2-hydroxy-1-methyl-3-(1H-1,2,4-triazol-1-yl)propyl]-7-(1H-1,2,4-triazol-1-yl)quinazolin-4(3H)-one Following a similar procedure to that described in example 17 but using the sodium salt of 1,2,4-triazole and heating the reaction at 120° C. overnight the title compound was obtained as a white solid: mp 236°–237° C.; $^1$H NMR (300 MHz, DMSO-d$_6$) δ (DMSO) 9.58 (s, 1H, triazole), 8.46 (s, 1H, N=CH—N), 8.38 (d, J=8.7, 1H, arom), 8.34 (s, 1H, triazole), 8.24 (d, J=1,5, 1H, arom), 8.19 (s, 1H, triazole), 8.11 (dd, J=2, J=8.5, 1H, arom), 7.55 (s, 1H, triazole), 7.3–7.2 (m, 2H, arom), 6.95 (dt, J$_d$=2.3, J$_t$=8.4, 1H, arom), 6.35 (s, 1H, OH), 5.86 (q, J=7.3, 1H, MeCH), 4.84 (d, J=14.5, 1H, CH(H)), 4.22 (d, J=14.5, 1H, CH(H)), 1.20 (d, J=7.3, 3H, CHMe); GC/MS 240 (N-ethylheterocycle, C$_{12}$H$_{11}$N$_5$O), 224 (Tr—CH$_2$COHAr, C$_{10}$H$_8$F$_2$N$_3$O); [α]$_D$=+61.7° (c 1, DMF). Analysis calculated for C$_{22}$H$_{18}$F$_2$N$_8$O$_2$: C 56.90; H 3.91; N 24.13. Found: C 55.61; H 3.80; N 23.68.

EXAMPLE 49

(1R,2R)-3-[2-(2,4-Difluorophenyl)-2-hydroxy-1-methyl-3-(1H-1,2,4-triazol-1-yl)propyl]-7-(4-morpholinyl)quinazolin-4(3H)-one Following the procedure described in example 40 but using morpholine the title product was obtained as a white solid: mp 196°–197° C.; $^1$H NMR (300 MHz, CDCl$_3$) δ (TMS) 8.49 (s, 1H, N=CH—N), 8.18 (d, J=9.0, 1H, arom), 7.75 (s, 1H, triazole), 7.73 (s, 1H, triazole), 7.5–7.4 (m, 1H, arom), 7.09 (dd, J=2.4, J=9.0, 1H, arom), 7.02 (d, J=2.4, 1H, arom), 6.9–6.6 (m, 2H, arom), 5.91 (dq, J$_d$=1.6, J$_q$=7.3, 1H, MeCH), 5.45 (d, J=1.6, 1H, OH), 5.17 (d, J=14.2, 1H, CH(H)), 4.03 (d, J=14.2, 1H, CH(H)), 3.88 (m, 4H, morpholine), 3.38 (m, 4H, morpholine), 1.27 (d, J=7.3, 3H, CHMe); GC/MS 259 (N-ethylheterocycle, C$_{14}$H$_{17}$N$_3$O$_2$), 224 (Tr—CH$_2$COHAr, C$_{10}$H$_8$F$_2$N$_3$O); [α]$_D$=−37.9° (c 1, CHCl$_3$). Analysis calculated for C$_{24}$H$_{24}$F$_2$N$_6$O$_3$: C 59.75; H 5.01; N 17.42. Found: C 59.62; H 4.97; N 17.21.

EXAMPLE 50

(1R,2R)-3-[2-(2,4-Difluorophenyl)-2-hydroxy-1-methyl-3-(1H-1,2,4-triazol-1-yl)propyl]-7-(methylthio)quinazolin-4(3H)-one Following the procedure described in example 17 but using the sodium salt of methanethiol and heating the reaction at 120° C. overnight the title compound was obtained as a white solid: mp 152°–153° C.; $^1$H NMR (300 MHz, CDCl$_3$) δ (TMS) 8.55 (s, 1H, N=CH—N), 8.17 (d, J=8.9, 1H, arom), 7.76 (s, 1H, triazole), 7.74 (s, 1H, triazole), 7.6–7.4 (m, 2H, arom), 7.36 (dd, J=1.7, J=8.5, 1H, arom), 6.9–6.7 (m, 2H, arom), 5.92 (dq, J$_d$=1.5, J$_q$=7.3, 1H, MeCH), 5.50 (d, J=1.5, 1H, OH), 5.17 (d, J=14.2, 1H, CH(H)), 4.02 (d, J=14.2, 1H, CH(H)), 2.59 (s, 3H, SMe), 1.29 (d, J=7.3, 3H, CHMe); GC/MS 224 (Tr—CH$_2$COHAr, C$_{10}$H$_8$F$_2$N$_3$O), 220 (N-ethylheterocycle, C$_{11}$H$_{12}$N$_2$OS); [α]$_D$=−53.6° (c 1, CHCl$_3$). Analysis calculated for C$_{21}$H$_{19}$F$_2$N$_5$O$_2$S: C 56.88; H 4.32; N 15.79; S 7.23. Found: C 56.48; H 4.39; N 15.33; S 7.52.

EXAMPLE 51

(1R,2R)-3-[2-(2,4-Difluorophenyl)-2-hydroxy-1-methyl-3-(1H-1,2,4-triazol-1-yl)propyl]-7-(methylsulfonyl)quinazolin-4(3H)-one A solution of the product obtained in example 50 (0.22 g, 0.49 mmol) in CH$_2$Cl$_2$ (10 mL) was treated with a dried (Na$_2$SO$_4$) solution of MCPBA (55%, 0.62 g, 1.98 mmol) in CH$_2$Cl$_2$ (10 mL) at 25° C. for 18 h. The solid formed was filtered, and the filtrate was then washed with 10% aqueous Na$_2$S$_2$O$_3$ solution, 1N NaOH and brine. The organic phase was dried over anhydrous Na$_2$SO$_4$, filtered, concentrated, purified by flash chromatography and recrystallized from EtOAc: ether to give the title product as a white solid (141 mg, 56%): mp 223°–224° C.; $^1$H NMR (300 MHz, CDCl$_3$) δ (TMS) 8.68 (s, 1H, N=CH—N), 8.53 (d, J=8.4, 1H, arom), 8.36 (d, J=1.6, 1H, arom), 8.03 (dd, J=1.6, J=8.3, 1H, arom), 7.77 (s, 1H, triazole), 7.74 (s, 1H, triazole), 7.48 (dt, J$_d$=6.4, J$_t$=8.8, 1H, arom), 6.9–6.7 (m, 2H, arom), 5.92 (dq, J$_d$=1.5, J$_q$=7.3, 1H, MeCH), 5.59 (d, J=1.5, 1H, OH), 5.15 (d, J=14.2, 1H, CH(H)), 4.00 (d, J=14.2, 1H, CH(H)), 3.13 (s, 3H, SO$_2$Me), 1.32 (d, J=7.3, 3H, CHMe); GC/MS 252 (N-ethylheterocycle, C$_{11}$H$_{12}$N$_2$O$_3$S), 224 (Tr—CH$_2$COHAr, C$_{10}$H$_8$F$_2$N$_3$O); [α]$_D$=+2.1° (c 0.5, CHCl$_3$). Analysis calculated for C$_{21}$H$_{19}$F$_2$N$_5$O$_4$S: C 53.05; H 4.03; N 14.73; S 6.74. Found: C 52.69; H 4.09; N 14.71; S 6.24.

EXAMPLE 52

(1R,2R)-7-Chloro-3-[2-(2,4-dichlorophenyl)-2-hydroxy-1-methyl-3-(1H-1,2,4-triazol-1-yl)propyl]quinazolin-4(3H)-one Following a similar procedure to that described in example 1 but using (2R,3R)-3-amino-2-(2,4-dichlorophenyl)-1-(1H-1,2,4-triazol-1-yl)-2-butanol (obtained as described in Konosu et al. *Chem. Pharm. Bull.* 1990, 38, 2476) the title compound was obtained as a white solid: mp 144°–146° C.; $^1$H NMR (300 MHz, CDCl$_3$) δ (TMS) 8.57 (s, 1H, N=CH—N), 8.26 (d, J=8.6, 1H, arom), 7.81 (s, 1H, triazole), 7.76 (d, J=2, 1H, arom), 7.73 (s, 1H, triazole), 7.62 (d, J=8.6, 1H, arom), 7.49 (dd, J=2, J=8.6, 1H, arom), 7.38 (d, J=2.2, 1H, arom), 7.17 (dd, J=2.2, J=8.6, 1H, arom), 6.40 (dq, J$_d$=1.7, J$_q$=7.3, 1H, MeCH), 5.74 (d, J=14.3, 1H, CH(H)) 5.64 (d, J=1.8, 1H, OH), 3.96 (d, J=14.3, 1H, CH(H)), 1.26 (d, J=7.3, 3H, CHMe); GC/MS 208 and 210 (N-ethylheterocycle, C$_{10}$H$_9$ClN$_2$O), 256 and 258 (Tr—CH$_2$COHAr, C$_{10}$H$_8$Cl$_2$N$_3$O); [α]$_D$=−46.6° (c 0.12, CHCl$_3$). Analysis calculated for C$_{20}$H$_{16}$Cl$_3$N$_5$O$_2$: C 51.69; H 3.47; N 15.07. Found: C 51.48; H 3.81; N 14.71.

EXAMPLE 53

(1R,2R)-3-[2-(2,4-Dichlorophenyl)-2-hydroxy-1-methyl-3-(1H-1,2,4-triazol-1-yl)propyl]-7-trifluoromethylquinazolin-4(3H)-one Following a similar procedure to that described in example 16 but using (2R,3R)-3-amino-2-(2,4- dichlorophenyl)-1-(1H-1,2,4-triazol-1-yl)-2-butanol the title compound was obtained as a white solid: mp 158°–160° C.; $^1$H NMR (300 MHz, CDCl$_3$) δ (TMS) 8.63 (s, 1H, N=CH—N), 8.45 (d, J=8.4, 1H, arom), 8.05 (s, 1H, arom), 7.81 (s, 1H, triazole), 7.76 (d, J=1.2, 1H, arom), 7.73 (s, 1H, triazole), 7.63 (d, J=8.6, 1H, arom), 7.39 (d, J=2.1, 1H, arom), 7.17 (dd, J=2.1, J=8.6, 1H, arom), 6.42 (dq, J$_d$=1.7, J$_q$=7.3, 1H, MeCH), 5.75 (d, J=14.3, 1H, CH(H)), 5.68 (d, J=1.8, 1H, OH), 3.96 (d, J=14.3, 1H, CH(H)), 1.28 (d, J=7.3,3H, CHMe); GC/MS 242 (N-ethylheterocycle, C$_{11}$H$_9$F$_3$N$_2$O), 256 and 258 (Tr—CH$_2$COHAr, C$_{10}$H$_8$Cl$_2$N$_3$O); [α]$_D$=−31.5° (c 0.2, CHCl$_3$). Analysis calculated for C$_{21}$H$_{16}$Cl$_2$F$_3$N$_5$O$_2$: C 50.62; H 3.24; N 14.05. Found: C 50.30; H 3.59; N 13.92.

EXAMPLE 54

(1R,2R)-6-(4-Chlorophenyl)-3-[2-(2,4-dichlorophenyl)-2-hydroxy-1-methyl-3-(1H-1,2,4-triazol-1-yl)propyl]thieno[3,2-d]pyrimidin-4(3H)-one Following a similar procedure to that described in example 31 but using (2R,3R)-3-amino-2-(2,4-dichlorophenyl)-1-(1H-1,2,4-triazol-1-yl)-2-butanol the title compound was obtained as a white solid: mp 132°–136° C.; $^1$H NMR (300 MHz, CDCl$_3$) δ (TMS) 8.59 (s, 1H, N=CH—N), 7.82 (s, 1H, triazole), 7.73 (s, 1H, triazole), 7.66 (d, J=8.2, 2H, arom), 7.63 (d, J=7.1, 1H, arom), 7.53 (d, J=0.5, 1H, thiophene), 7.44 (d, J=8.2, 2H, arom), 7.39 (d, J=1.6, 1H, arom), 7.17 (dd, J=1.6, J=8.6, 1H, arom), 6.46 (dq, J$_d$=1.7, J$_q$=7.3, 1H, MeCH), 5.80 (d, J=14.4, 1H, CH(H)), 5.65 (d, J=1.6, 1H, OH), 3.97 (d, J=14.4, 1H, CH(H)), 1.28 (d, J=7.3, 3H, CHMe); GC/MS 290 (N-ethylheterocycle, C$_{14}$H$_{11}$ClN$_2$OS), 256 and 258 (Tr—CH$_2$COHAr, C$_{10}$H$_8$C$_{12}$N$_3$O); [α]$_D$=−19.0° (c 0.2, CHCl$_3$). Analysis calculated for C$_{24}$H$_{18}$Cl$_3$N$_5$O$_2$S: C 52.71; H 3.32; N 12.81; S 5.86. Found: C 51.40; H 3.27; N 12.04; S 5.20.

EXAMPLE 55

(1R,2R)-4-[3-[2-(2,4-Dichlorophenyl)-2-hydroxy-1-methyl-3-(1H-1,2,4-triazol-1 -yl)propyl]-4-oxo-3,4-dihydrothieno[3,2-d]pyrimidin-6-yl]benzonitrile Following a similar procedure to that described in example 32 but using (2R,3R)-3-amino-2-(2,4-dichlorophenyl)-1-(1H-1,2,4-triazol-1-yl)-2-butanol the title compound was obtained as an off-white solid: mp 133°–138° C.; $^1$H NMR (300 MHz, CDCl$_3$) δ (TMS) 8.61 (s, 1H, N=CH—N), 7.9–7.7 (complex m, triazole, arom), 7.65 (s, 1H, thiophene), 7.52 (d, J=8.6, 2H, arom), 7.39 (d, J=2.0, 1H, arom), 7.17 (dd, J=2.0, J=8.6, 1H, arom), 6.46 (dq, J$_d$=1.5, J$_q$=7.3, 1H, MeCH), 5.78 (d, J=14.3, 1H, CH(H)), 5.67 (d, J=1.5, 1H, OH), 3.97 (d, J=14.3, 1H, CH(H)), 1.28 (d, J=7.3, 3H, CHMe); MS 281 (N-ethylheterocycle, C$_{15}$H$_{11}$N$_3$OS), 256 and 258 (Tr—CH$_2$COHAr, C$_{10}$H$_8$Cl$_2$N$_3$O); [α]$_D$=−50° (c 0.1, CHCl$_3$).

EXAMPLE 56

(1R,2R)-7-Amino-3-[2-(2,4-difluorophenyl)-2-hydroxy-1-methyl-3-(1H-1,2,4-triazol-1-yl)propyl]-6-fluoro quinazolin-4(3H)-one Following a similar procedure to that described in example 40 but using (1R,2R)-6,7-difluoro-3-[2-(2,4-difluorophenyl)-2-hydroxy-1-methyl-3-(1H-1,2,4-triazol-1-yl)propyl]quinazolin-4(3H)-one (obtained in example 15) and NH$_4$OH the title compound was obtained as a white solid: mp 124°–125° C.; $^1$H NMR (300 MHz, CDCl$_3$) δ (TMS) 8.45 (s, 1H, N=CH—N), 7.86 (d, J=11, 1H, arom), 7.76 (s, 1H, triazole), 7.72 (s, 1H, triazole), 7.6–7.4 (m, 1H, arom), 6.97 (d, J=8.0, 1H, arom), 6.9–6.7 (m, 2H, arom), 5.89 (dq, J$_d$=1.7, J$_q$=7.3, 1H, MeCH), 5.46 (d, J=1.7, 1H, OH), 5.15 (d, J=14.2, 1H, CH(H)), 4.43 (broad s, 2H, NH$_2$), 4.01 (d, J=14.2, 1H, CH(H)), 1.26 (d, J=7.3, 3H, CHMe); GC/MS 224 (Tr—CH$_2$COHAr, C$_{10}$H$_8$F$_2$N$_3$O), 207 (N-ethylheterocycle, C$_{10}$H$_{10}$FN$_3$O); [α]$_D$=−0.31° (c 1, MeOH). Analysis calculated for C$_{20}$H$_{17}$F$_3$N$_6$O$_2$.H$_2$O: C 53.57; H 4.27; N 18.74. Found: C 54.16; H 4.29; N 17.42.

EXAMPLE 57

(1R,2R)-N-[3-[2-(2,4-Difluorophenyl)-2-hydroxy-1-methyl-3-(1H-1,2,4-triazol-1-yl)propyl]-6-fluoro-4-oxo-3,4-dihydroquinazolin-7-yl]-2,2,2-trifluoroacetamide A solution of the product obtained in the preceding example (500 mg, 1.16 mmol) in pyridine (5 mL) was treated with trifluoroacetic anhydride (488 mg, 2.3 mmol) at 0° C. for 1 h. Next aqueous Na$_2$CO$_3$ solution was added, pyridine was removed in vacuo and the residue was partitioned between water and CHCl$_3$. The organic layer was separated, dried over Na$_2$SO$_4$, filtered and concentrated to an oil that was purified by flash chromatography to give the title product as a white solid (412 mg, 67%): mp 130°–132° C.; $^1$H NMR (300 MHz, CDCl$_3$) δ (TMS) 8.77 (d, J=7, 1H, arom), 8.58 (s, 1H, N=CH—N), 8.33 (broad s, 1H, NH), 8.07 (d, J=10.6, 1H, arom), 7.76 (s, 1H, triazole), 7.74 (s, 1H, triazole), 7.49 (dt, J$_d$=6.5, J$_t$=9, 1H, arom), 6.9–6.7 (m, 2H, arom), 5.91 (dq, J$_d$=1.5, J$_q$=7.3, 1H, MeCH), 5.56 (d, J=1.7, 1H, OH), 5.13 (d, J=14.2, 1H, CH(H)), 4.02 (d, J=14.2, 1H, CH(H)), 1.30 (d, J=7.3, 3H, CHMe); GC/MS 303 (N-ethylheterocycle, C$_{12}$H$_9$F$_4$N$_3$O$_2$), 224 (Tr—CH$_2$COHAr, C$_{10}$H$_8$F$_2$N$_3$O); [α]$_D$=−38.4° (c 1, CHCl$_3$). Analysis calculated for C$_{22}$H$_{16}$F$_6$N$_6$O$_3$: C 50.20; H 3.06; N 15.97. Found: C 49.75; H 2.97; N 15.48.

EXAMPLE 58

(1R,2R)-7-Aminocarbonyl-3-[2-(2,4-difluorophenyl)-2-hydroxy-1-methyl-3-(1H-1,2,4-triazol-1-yl)propyl]quinazolin-4(3H)-one A solution of (1R,2R)-7-cyano-3-[2-(2,4-difluorophenyl)-2-hydroxy-1-methyl-3-(1H-1,2,4-triazol-1-yl)propyl]quinazolin-4(3H)-one (obtained in example 2, 500 mg, 1.2 mmol) in MeOH (5 mL) and CHCl$_3$ (5 mL) was cooled to 0° C. and HCl gas was bubbled until saturation (1.5 h). The mixture was allowed to stand at 0° C. overnight and was then concentrated and the residue was slowly added to aqueous K$_2$CO$_3$ solution (2.5 g). The yellowish precipitate formed was filtered, dried, taken up in methanol and allowed to react with sulfamide (350 mg, 3.6 mmol) at reflux for 3 h. The reaction mixture was then concentrated and partitioned between water and CHCl$_3$. The organic layer was separated, dried over Na$_2$SO$_4$, filtered, concentrated and the resulting residue, whose thin layer chromatography showed the presence of three different compounds, was flash chromatographed. The first compound to elute was identified as the methyl imidate. The second compound to elute was the amide (title compound), the physical parameters of which are as follows: mp 235°–236° C.; $^1$H NMR (300 MHz, CDCl$_3$) δ (TMS) 8.63 (s, 1H, N=CH—N), 8.42 (d, J=8.2, 1H, arom), 8.13 (d, J=1.5, 1H, arom), 7.98 (dd, J=8.2, J=1.5, 1H, arom), 7.77 (s, 1H, triazole), 7.74 (s, 1H, triazole), 7.48

(dt, $J_d$=6.4, $J_t$=8.8, 1H, arom), 6.9–6.8 (m, 2H, arom), 6.3 (broad s, 2H, NH$_2$), 5.92 (dq, $J_d$=1.2, $J_q$=7.3, 1H, MeCH), 5.56 (d, J=1.3, 1H, OH), 5.16 (d, J=14.1, 1H, CH(H)), 4.03 (d, J=14.1, 1H, CH(H)), 1.32 (d, J=7.3, 3H, CHMe); GC/MS 224 (Tr—CH$_2$COHAr, C$_{10}$H$_8$F$_2$N$_3$O), 216 (N-ethylheterocycle-1, C$_{11}$H$_{11}$N$_3$O$_2$).

EXAMPLE 59

(1R,2R)-7-[(Aminosulfonylamino)iminomethyl]-3-[2-(2,4-difluorophenyl)-2-hydroxy-1-methyl-3-(1H-1,2,4-triazol-1-yl)propyl]quinazolin-4(3H)-one Proceeding with the flash chromatography of example 58, a third compound eluted which was identified as the title compound (80 mg, 13%) and which was obtained as a white solid: mp 202°–206° C.; $^1$H NMR (300 MHz, MeOH-d$_4$) δ (MeOH) 8.59 (s, 1H, N=CH—N), 8.39 (d, J=8.4, 1H, arom), 8.19 (dd, J=1.5, J=8.5, 1H, arom), 8.17 (s, 1H, triazole), 8.02 (dd, J=1.7, J=8.4, 1H, arom), 7.63 (s, 1H, triazole), 7.42 (dt, $J_t$=6.5, $J_d$=9, 1H, arom), 7.05 (ddd, $J_d$=2.5, $J_d$=8.5, $J_d$=14, 1H, arom), 6.89 (dt, $J_d$=2.5, $J_t$=8.5, 1H, arom), 6.06 (q, J=7.3, 1H, MeCH), 5.06 (d, J=14.2, 1H, CH(H)), 4.22 (d, J=14.2, 1H, CH(H)), 1.31 (d, J=7.3, 3H, CHMe); [α]$_D$=+35.5° (c 0.2, MeOH). Analysis calculated for C$_{21}$H$_{20}$F$_2$N$_8$O$_4$S: C 48.65; H 3.89; N 21.61; S 6.18. Found: C 48.77; H 4.24; N 20.19; S 5.49.

EXAMPLE 60

(1R,2R)-3-[2-(2,4-Difluorophenyl)-2-hydroxy-1-methyl-3-(1H-1,2,4-triazol-1-yl)propyl]-7-(phenylthio)quinazolin-4(3H)-one Following the procedure described in example 50 but using the sodium salt of thiophenol the title compound was obtained as a white solid: mp 84°–87° C.; $^1$H NMR (300 MHz, CDCl$_3$) δ (TMS) 8.50 (s, 1H, N=CH—N), 8.17 (d, J=8.5, 1H, arom), 7.75 (s, 1H, triazole), 7.76 (s, 1H, triazole), 7.6–7.3 (m, 8H, arom), 6.9–6.7 (m, 2H, arom), 5.90 (dq, $J_d$=1.5, $J_q$=7.3, 1H, MeCH), 5.48 (d, J=1.5, 1H, OH), 5.15 (d, J=14.2, 1H, CH(H)), 3.99 (d, J=14.2, 1H, CH(H)), 1.27 (d, J=7.3, 3H, CHMe); GC/MS 282 (N-ethylheterocycle, C$_{16}$H$_{14}$N$_2$OS), 224 (Tr—CH$_2$COHAr, C$_{10}$H$_8$F$_2$N$_3$O); [α]$_D$=−49.5° (c 1, CHCl$_3$). Analysis calculated for C$_{26}$H$_{21}$F$_2$N$_5$O$_2$S: C 61.77; H 4.19; N 13.85; S 6.34. Found: C 61.34; H 4.51; N 13.04; S 6.31.

EXAMPLE 61

(1R,2R)-3-[2-(2,4-Difluorophenyl)-2-hydroxy-1-methyl-3-(1H-1,2,4-triazol-1-yl)propyl]-7-phenylsulfonylquinazolin-4(3H)-one Following the procedure described in example 51 but using the compound obtained in the preceding example, the title compound was obtained as a white solid: mp 125°–130° C.; $^1$H NMR (300 MHz, CDCl$_3$) δ (TMS) 8.63 (s, 1H, N=CH—N), 8.44 (d, J=8.4, 1H, arom), 8.35 (d, J=1.6, 1H, arom), 8.02 (d, J=8.3, 3H, arom), 7.77 (s, 1H, triazole), 7.73 (s, 1H, triazole), 7.6–7.4 (m, 4H, arom), 6.9–6.7 (m, 2H, arom), 5.90 (dq, $J_d$=1.5, $J_q$=7.3, 1H, MeCH), 5.55 (d, J=1.5, 1H, OH), 5.12 (d, J=14.2, 1H, CH(H)), 3.94 (d, J=14.2, 1H, CH(H)), 1.28 (d, J=7.3, 3H, CHMe); GC/MS 314 (N-ethylheterocycle, C$_{16}$H$_{14}$N$_2$O$_3$S), 224 (Tr—CH$_2$COHAr, C$_{10}$H$_8$F$_2$N$_3$O); [α]$_D$=+7.0° (c 1, CHCl$_3$). Analysis calculated for C$_{26}$H$_{21}$F$_2$N$_5$O$_4$S: C 58.10; H 3.94; N 13.03; S 5.96. Found: C 57.83; H 4.03; N 12.79; S 5.59.

EXAMPLE 62

(1R,2R)-3-[2-(2,4-Difluorophenyl)-2-hydroxy-1-methyl-3-(1H-1,2,4-triazol-1-yl)propyl]-6-[4-[(hydroxyamino)iminomethyl]phenyl]thieno[3,2-d]pyrimidin-4(3H)-one To a solution of Na$_2$CO$_3$ (0.84 g, 7.92 mmol) in a mixture of H$_2$O (8 mL) and THF (30 mL) was added (1R,2R)-4-[3-[2-(2,4-difluorophenyl)-2-hydroxy-1-methyl-3-(1H-1,2,4-triazol-1-yl)propyl]-4-oxo-3,4-dihydrothieno[3,2-d]pyrimidin-6-yl]benzonitrile (0.5 g, 0.99 mmol, obtained in example 32) and hydroxylamine hydrochloride (0.35 g, 1.95 mmol). The mixture was stirred at reflux overnight, concentrated and the aqueous residue was extracted with CHCl$_3$. The organic phase was separated, dried over Na$_2$SO$_4$, filtered and the filtrate concentrated to a solid which was purified by flash chromatography to give the title compound as a pale yellow solid (325 mg, 61%): mp 246°–247° C.; $^1$H NMR (300 MHz, MeOH-d$_4$) δ (MeOH) 8.60 (s, 1H, N=CH—N), 8.18 (s, 1H, triazole), 7.86 (d, J=8.5, 2H, arom), 7.78 (d, J=8.5, 2H, arom), 7.71 (s, 1H, triazole), 7.66 (s, 1H, thiophene), 7.43 (dt, $J_t$=6.5, $J_d$=9, 1H, arom), 7.06 (ddd, $J_d$=2.5, $J_d$=8.5, $J_d$=14, 1H, arom), 6.89 (dt, $J_d$=2.5, $J_t$=8.5, 1H, arom), 6.09 (q, J=7.3, 1H, MeCH), 5.09 (d, J=14.2, 1H, CH(H)), 4.19 (d, J=14.2, 1H, CH(H)), 1.32 (d, J=7.3, 3H, CHMe); MS 314 (N-ethylheterocycle, C$_{15}$H$_{14}$N$_4$O$_2$S), 224 (Tr—CH$_2$COHAr, C$_{10}$H$_8$F$_2$N$_3$O); [α]$_D$=+74.9° (c 1, MeOH). Analysis calculated for C$_{25}$H$_{21}$F$_2$N$_7$O$_3$S: C 55.86; H 3.94; N 18.24; S 5.96. Found: C 55.10; H 3.84; N 17.72; S 5.69.

EXAMPLE 63

(1R,2R)-3-[2-(2,4-Difluorophenyl)-2-hydroxy-1-methyl-3-(1H-1,2,4-triazol-1-yl)propyl]-6-[4-[imino(methoxy)methyl]phenyl]thieno[3,2-d]pyrimidin-4(3H)-one To a cooled (0° C.) solution of (1R,2R)-(4-[3-[2-(2,4-difluorophenyl)-2-hydroxy-1-methyl-3-(1H-1,2,4-triazol-1-yl)propyl]-4-oxo-3,4-dihydrothieno[3,2-d]pyrimidin-6-yl]benzonitrile (1.03 g, 2.04 mmol) (obtained in example 32) in MeOH (25 mL) and CHCl$_3$ (5 mL) was bubbled HCl gas until saturation. The reaction mixture was allowed to stand at 0° C. overnight, and was then concentrated and poured to aqueous K$_2$CO$_3$ solution. CHCl$_3$ was added, the organic phase was separated and the aqueous phase was reextracted with CHCl$_3$. The combined organic extracts were washed with water and brine, dried over Na$_2$SO$_4$, filtered and concentrated to give the title compound as a white solid (1.03 g, 94%): mp 194°–201° C.; $^1$H NMR (300 MHz, CDCl$_3$) δ (TMS) 8.60 (s, 1H, N=CH—N), 7.78 (s, 1H, triazole), 7.77 (s, 4H, arom), 7.74 (s, 1H, triazole), 7.60 (s, 1H, thiophene), 7.49 (dt, $J_d$=6.4, $J_t$=8.8, 1H, arom), 6.9–6.7 (m, 2H, arom), 5.98 (q, J=7.3, 1H, MeCH), 5.56 (broad s, 1H, OH), 5.20 (d, J=14.2, 1H, CH(H)), 4.02 (d, J=14.2, 1H, CH(H)), 3.97 (s, 3H, OCH$_3$),1.32 (d, J=7.3, 3H, CHMe).

EXAMPLE 64

(1R,2R)-3-[2-(2,4-Difluorophenyl)-2-hydroxy-1-methyl-3-(1H-1,2,4-triazol-1-yl)propyl]-6-[4-[ethoxy(imino)methyl]phenyl]thieno[3,2-d]pyrimidin-4(3H)-one Following the procedure described in the preceding example but carrying out the reaction in EtOH the title compound was obtained as a white solid: mp 158°–161° C.; $^1$H NMR (300 MHz, CDCl$_3$) δ (TMS) 8.60 (s, 1H, N=CH—N), 7.86 (d, $J_t$=8.2, 2H, arom), 7.78 (s, 1H, triazole), 7.75 (d, $J_t$=8.2, 2H, arom), 7.74 (s, 1H, triazole), 7.60 (s, 1H, thiophene), 7.49 (dt, $J_d$=6.4, $J_t$=8.8, 1H, arom), 6.9–6.7 (m, 2H, arom), 5.98 (dq, $J_d$=1.6, $J_q$=7.3, 1H, MeCH), 5.55 (d, J=1.6, 1H, OH), 5.20 (d, J=14.2, 1H, CH(H)), 4.37 (q, J=7.3, 2H, OCH$_2$CH$_3$), 4.02 (d, J=14.2, 1H, CH(H)), 1.45 (t, J=7.3, 3H, OCH$_2$CH$_3$), 1.32 (d, J=7.3, 3H, CHMe); [α]$_D$=+9.5° (c 1, CHCl$_3$). Analysis calculated for $C_{27}H_{24}F_2N_6O_3S$: C 58.90; H 4.39; N 15.24; S 5.81. Found: C 58.30; H 4.46; N 14.57; S 5.50.

EXAMPLE 65

(1R,2R)-6-[4-[Cyanoamino(imino)methyl]phenyl]-3-[2-(2,4-difluorophenyl)-2-hydroxy-1-methyl-3-(1H-1,2,4-triazol-1-yl)propyl]thieno[3,2-d]pyrimidin-4(3H)-one A solution of (1R,2R)-3-[2-(2,4-difluorophenyl)-2-hydroxy-1-methyl-3-(1H-1,2,4-triazol-1-yl)propyl]-6-[4-[imino(methoxy)methyl]phenyl]thieno[3,2-d]pyrimidin-4(3H)-one (0.35 mg, 0.652 mmol) (obtained in example 63) and $NH_2CN$ (140 mg, 3.26 mmol) in MeOH (15 mL) was refluxed overnight. The solvent was removed by concentration and the residue was partitioned between $CHCl_3$ and 10% $NaHCO_3$ solution. The organic phase was separated, dried over $Na_2SO_4$, filtered, concentrated and purified by flash chromatography to give the title compound as a white solid: mp 275°–278° C.; $^1$H NMR (300 MHz, MeOH-d4) δ (MeOH) 8.61 (s, 1H, N=CH—N), 8.18 (s, 1H, triazole), 8.02 (d, J=8.5, 2H, arom), 7.95 (d, J=8.5, 2H, arom), 7.81 (s, 1H, thiophene), 7.66 (s, 1H, triazole), 7.43 (dt, $J_t$=6.5, $J_d$=9, 1H, arom), 7.08 (ddd, $J_d$=2.5, $J_d$=8.5, $J_d$=14, 1H, arom), 6.89 (dt, $J_d$=2.5, $J_t$=8.5, 1H, arom), 6.09 (q, J=7.3, 1H, MeCH), 5.09 (d, J=14.2, 1H, CH(H)), 4.19 (d, J=14.2, 1H, CH(H)), 1.33 (d, J=7.3, 3H, CHMe); $[α]_D$=+43.0° (c 0.25, MeOH). Analysis calculated for $C_{26}H_{20}F_2N_8O_2S.H_2O$: C 55.31; H 3.93; N 19.85; S 5.68. Found: C 55.06; H 3.74; N 18.57; S 5.28.

EXAMPLE 66

(1R,2R)-6-[4-(Aminocarbonyl)phenyl]-3-[2-(2,4-difluorophenyl)-2-hydroxy-1-methyl-3-(1H-1,2,4-triazol-1-yl)propyl]thieno[3,2-d]pyrimidin-4(3H)-one A solution of (1R,2R)-3-[2-(2,4-difluorophenyl)-2-hydroxy-1-methyl-3-(1H-1,2,4-triazol-1-yl)propyl]-6-[4-imino(methoxy)methyl]phenyl]thieno[3,2-d]pyrimidin-4(3H)-one (0.35 g, 0.652 mmol) (obtained in example 63) and 1N HCl (2 mL) in MeOH (15 mL) was allowed to react at room temperature overnight. The solvent was removed by concentration and the residue was partitioned between $CHCl_3$ and 10% $NaHCO_3$ solution. The organic phase was separated, dried over $Na_2SO_4$, filtered, concentrated and purified by flash chromatography to give the title compound as a white solid: mp 280°–285° C.; $^1$H NMR (300 MHz, $CDCl_3$) δ (TMS) 8.61 (s, 1H, N=CH—N), 7.92 (d, $J_t$=8.4, 2H, arom), 7.81 (d, $J_t$=8.4, 2H, arom), 7.78 (s, 1H, triazole), 7.74 (s, 1H, triazole, 7.63 (s, 1H, thiophene), 7.49 (dt, $J_d$=6.4, $J_t$=8.8, 1H, arom), 6.9–6.7 (m, 2H, arom), 6.2–5.5 (broad signal, 2H, NH$_2$), 5.98 (dq, $J_d$=1.6, $J_q$=7.3, 1H, MeCH), 5.56 (d, J=1.6, 1H, OH), 5.20 (d, J=14.2, 1H, CH(H)), 4.03 (d, J=14.2, 1H, CH(H)), 1.32 (d, J=7.3, 3H, CHMe); MS 299 (N-ethylheterocycle, $C_{15}H_{13}N_3O_2S$), 224 (Tr—$CH_2COHAr$, $C_{10}H_8F_2N_3O$); $[α]_D$=+63.6° (c 1, MeOH).

EXAMPLE 67

(1R,2R)-3-[2-(2,4-Difluorophenyl)-2-hydroxy-1-methyl-3-(1H-1,2,4-triazol-1-yl)propyl]-6-[4-[imino(methoxyamino)methyl]phenyl]thieno[3,2-d]pyrimidin-4(3H)-one Following the procedure described in example 65 but using O-methylhydroxylamine the title compound was obtained as a white solid: mp 125°–128° C.; $^1$H NMR (300 MHz, $CDCl_3$) δ (TMS) 8.60 (s, 1H, N=CH—N), 7.78 (s, 1H, triazole), 7.74 (s, 5H, triazole, arom), 7.57 (s, 1H, thiophene), 7.49 (dt, $J_d$=6.4, $J_t$=8.8, 1H, arom), 6.9–6.7 (m, 2H, arom), 5.98 (dq, $J_d$=1.6, $J_q$=7.3, 1H, MeCH), 5.54 (d, J=1.5, 1H, OH), 5.20 (d, J=14.2, 1H, CH(H)), 4.83 (broad s, 2H), 4.02 (d, J=14.2, 1H, CH(H)), 3.95 (s, 3H, OMe), 1.32 (d, J=7.3, 3H, CHMe); MS 328 (N-ethylheterocycle, $C_{16}H_{16}N_4O_2S$), 224 (Tr—$CH_2COHAr$, $C_{10}H_8F_2N_3O$); $[α]_D$=+8.4° (c 0.5, $CHCl_3$). Analysis calculated for $C_{26}H_{23}F_2N_7O_3S$: C 56.62; H 4.20; N 17.78; S 5.81. Found: C 56.66; H 4.03; N 17.45; S 5.43.

EXAMPLE 68

(1R,2R)-6-[4-[Acetoxyamino(imino)methyl]phenyl]-3-[2-(2,4-difluorophenyl)-2-hydroxy-4-methyl-3-(1H-1,2,4-triazol-1-yl)propyl]thieno[3,2-d]pyrimidin-4(3H)-one A solution of the product obtained in example 62 (150 mg, 0.27 mmol) in $CHCl_3$ (10 mL) was treated with triethylamine (33 μL, 0.33 mmol) and acetyl chloride (25 μL, 0.32 mmol) at 25° C. for 18 h. Next 10% aqueous $NaHCO_3$ solution was added and the aqueous layer was separated. The organic phase was washed with water, dried over $Na_2SO_4$, filtered, concentrated and purified by flash chromatography to give the title product as a white solid: mp 140°–146° C.; $^1$H NMR (300 MHz, $CDCl_3$) δ (TMS) 8.61 (s, 1H, N=CH—N), 7.81 (d, $J_t$=8.6, 2H, arom), 7.78 (s, 1H, triazole), 7.76 (d, $J_t$=8.2, 2H, arom), 7.74 (s, 1H, triazole), 7.59 (s, 1H, thiophene), 7.49 (dt, $J_d$=6.5, $J_t$=8.8, 1H, arom), 6.9–6.7 (m, 2H, arom), 5.99 (dq, $J_d$=1.6, $J_q$=7.3, 1H, MeCH), 5.55 (d, J=1.6, 1H, OH), 5.20 (d, J=14.2, 1H, CH(H)), 5.13 (broad s, 2H), 4.05 (d, J=14.2, 1H, CH(H)), 2.27 (s, 3H, COMe), 1.32 (d, J=7.3, 3H, CHMe); MS 338 (N-ethylheterocycle (—$H_2O$), $C_{17}H_{14}N_4O_2S$), 224 (Tr—$CH_2COHAr$, $C_{10}H_8F_2N_3O$); $[α]_D$=+2.0° (c 1, $CHCl_3$).

EXAMPLE 69

(1R,2R)-3-[2-(2,4-Difluorophenyl)-2-hydroxy-1-methyl-3-(1-H-1,2,4-triazol-1-yl)propyl]-6-[4-(4,5-dihydrooxazol-2-yl)phenyl]thieno[3,2-d]pyrimidin-4(3H)-one Following the procedure described in example 65 but using 2-ethanolamine the title product was obtained as a white solid: mp 235°–236° C.; $^1$H NMR (300 MHz, $CDCl_3$) δ (TMS) 8.61 (s, 1H, N=CH—N), 8.04 (d, $J_t$=8.4, 2H, arom), 7.78 (s, 1H, triazole), 7.76 (d, J=8.4, 2H, arom), 7.74 (s, 1H, triazole), 7.62 (s, 1H, thiophene), 7.49 (dt, $J_d$=6.5, $J_t$=8.8, 1H, arom), 6.9–6.7 (m, 2H, arom), 5.98 (dq, $J_d$=1.6, $J_q$=7.3, 1H, MeCH), 5.55 (s, 1H, OH), 5.20 (d, J=14.2, 1H, CH(H)), 4.47 (t, J=9.8, 2H, NCH$_2$CH$_2$O), 4.11 (t, J=9.8, 2H, NCH$_2$CH$_2$O), 4.02 (d, J=14.2, 1H, CH(H)), 1.32 (d, J=7.3, 3H, CHMe); MS 325 (N-ethylheterocycle group, $C_{17}H_{15}N_3O_2S$), 224 (Tr—$CH_2COHAr$, $C_{10}H_8F_2N_3O$); $[α]_D$=+19.0° (c 1, $CHCl_3$). Analysis calculated for $C_{27}H_{22}F_2N_6O_3S$: C 59.12; H 4.04; N 15.32; S 5.84. Found: C 58.43; H 4.04; N 14.67; S 5.47.

EXAMPLE 70

(1R,2R)-6-[4-[(2-Aminoethylamino)(imino)methyl]phenyl]-3-[2-(2,4-difluorophenyl)-2-hydroxy-1-methyl-3-(1H-1,2,4-triazol-1-yl)propyl]thieno[3,2-d]pyrimidin-4(3H)-one Following the procedure described in example 58 but using ethylenediamine the title product was obtained as a yellowish solid: mp 154°–161° C.; $^1$H NMR (300 MHz, CDCl$_3$) δ (TMS) 8.61 (s, 1H, N═CH—N), 7.88 (d, J$_t$=8.5, 2H, arom), 7.78 (s, 1H, triazole), 7.76 (d, J=8.5, 2H, arom), 7.74 (s, 1H, triazole), 7.64 (s, 1H, thiophene), 7.49 (dt, J$_d$=6.5, J$_t$=8.8, 1H, arom), 6.9–6.7 (m, 2H, arom), 5.98 (dq, J$_d$=1.6, J$_q$=7.3, 1H, MeCH), 5.55 (s, 1H, OH), 5.20 (d, J=14.2, 1H, CH(H)), 4.07 (t, J=9.6, 2H, NCH$_2$CH$_2$NH$_2$), 4.02 (d, J=14.2, 1H, CH(H)), 3.60 (broad t, J=9.6, 2H, NCH$_2$CH$_2$NH$_2$), 1.32 (d, J=7.3, 3H, CHMe); MS 324 (N-ethylheterocycle (—NH$_3$), C$_{17}$H$_{16}$N$_4$OS), 224 (Tr—CH$_2$COHAr, C$_{10}$H$_8$F$_2$N$_3$O); [α]$_D$=+0.1° (c 0.15, CHCl$_3$).

EXAMPLE 71

(1R,2R)-7-Benzylamino-3-[2-(2,4-difluorophenyl)-2-hydroxy-1-methyl-3-(1H-1,2,4-triazol-1-yl)propyl]quinazolin-4(3H)-one Following the procedure described in example 40 but using benzylamine the title compound was obtained as a white solid: mp 100°–107° C.; $^1$H NMR (300 MHz, CDCl$_3$) δ (TMS) 8.45 (s, 1H, N═CH—N), 8.09 (d, J=8.5, 1H, arom), 7.76 (s, 1H, triazole), 7.73 (s, 1H, triazole), 7.48 (dt, J$_d$=6.4, J$_t$=8.8, 1H, arom), 7.5–7.3 (m, 5H, arom), 6.9–6.7 (m, 4H, arom), 5.90 (dq, J$_d$=1.5, J$_q$=7.3, 1H, MeCH), 5.42 (d, J=1.5, 1H, OH), 5.17 (d, J=14.2, 1H, CH(H)), 4.72 (broad t, J=4.8, 1H, NH), 4.47 (d, J=5.5, 2F, NCH$_2$), 4.03 (d, J=14.2, 1H, CH(H)), 1.26 (d, J=7.3, 3H, CHMe); GC/MS 279 (N-ethylheterocycle, C$_{17}$H$_{17}$N$_3$O), 224 (Tr—CH$_2$COHAr, C$_{10}$H$_8$F$_2$N$_3$O); [α]$_D$=−32.3° (c 1, CHCl$_3$). Analysis calculated for C$_{27}$H$_{24}$F$_2$N$_6$O$_2$: C 64.53; H 4.81; N 16.72. Found: C 64.53; H 4.86; N 16.93.

EXAMPLE 72

(1R,2R)-7-Amino-3-[2-(2,4-difluorophenyl)-2-hydroxy-1-methyl-3-(1H-1,2,4-triazol-1-yl)propyl]quinazolin-4(3H)-one To a solution of the product obtained in the preceding example (1.45 g, 2.8 mmol) in MeOH (10 mL) was added 10% Pd/C (250 mg) and a solution of ammonium formate (700 mg, 11.2 mmol) in H$_2$O (2.5 mL). The mixture was refluxed for 24 h and was then filtered through celite. The filtrate was then concentrated to give the title product as an off-white solid (1.16 g, 93%): mp 103°–109° C.; $^1$H NMR (300 MHz, MeOH-d$_4$) δ (MeOH) 8.39 (s, 1H, N═CH—N), 8.17 (s, 1H, triazole), 7.98 (d, J=8.7, 1H, arom), 7.63 (s, 1H, triazole), 7.5–7.2 (m, 2H, arom), 7.03 (ddd, J$_d$=2.5, J$_d$=8.5, J$_d$=14, 1H, arom), 6.9–6.8 (m, 2H, arom), 6.03 (q, J=7.3, 1H, MeCH), 5.06 (d, J=14.2, 1H, CH(H)), 4.14 (d, J=14.2, 1H, CH(H)), 1.26 (d, J=7.3, 3H, CHMe); CC/MS 224 (Tr—CH$_2$COHAr, C$_{10}$H$_8$F$_2$N$_3$O), 189 (N-ethylheterocycle, C$_{10}$H$_{11}$N$_3$O); [α]$_D$=−11.6° (c 0.5, CHCl$_3$). Analysis calculated for C$_{20}$H$_{18}$F$_2$N$_6$O$_2$: C 58.25; H 4.40; N 20.38. Found: C 57.57; H 4.53; N 18.43.

EXAMPLE 73

(1R,2R)-7-Bromo-3-[2-(2,4-difluorophenyl)-2-hydroxy-1-methyl-3-(1H-1,2,4-triazol-1-yl)propyl]quinazolin-4(3H)-one To a cooled (0° C.) solution of the product obtained in the preceding example (300 mg, 0.7 mmol) in 48% HBr (3 mL) was added a solution of NaNO$_2$ (48 mg, 0.7 mmol) in H$_2$O (0.5 mL). The mixture was poured to a mixture of CuBr (55 mg, 0.4 mmol) in 48% HBr (I mL). The reaction mixture was then refluxed for 2 h. Next, H$_2$O and EtOAc were added, the layers were separated and the organic phase was washed with 1N NaOH and with brine, dried over Na$_2$SO$_4$, filtered, concentrated and purified by flash chromatography to give the title product as a white solid (145 mg, 43%): mp 109°–112° C.; $^1$H NMR (300 MHz, CDCl$_3$) δ (TMS) 8.58 (s, 1H, N═CH—N), 8.19 (d, J=8.5, 1H, arom), 7.94 (d, J=1.8, 1H, arom), 7.76 (s, 1H, triazole), 7.74 (s, 1H, triazole), 7.64 (dd, J=1.8, J=8.5, 1H, arom), 7.48 (dt, J$_d$=6.4, J$_t$=8.8, 1H, arom), 6.9–6.7 (m, 2H, arom), 5.91 (dq, J$_d$=1.5, J$_q$=7.3, 1H, MeCH), 5.54 (d, J=1.5, 1H, OH), 5.14 (d, J=14.2, 1H, CH(H)), 4.00 (d, J=14.2, 1H, CH(H)), 1.29 (d, J=7.3, 3H, CHMe); GC/MS 252 and 254 (N-ethylheterocycle, C$_{10}$H$_9$BrN$_2$O), 224 (Tr—CH$_2$COHAr, C$_{10}$H$_8$F$_2$N$_3$O); [α]$_D$=−10.8° (c 1, CHCl$_3$). Analysis calculated for C$_{20}$H$_{16}$BrF$_2$N$_5$O$_2$: C 50.44; H 3.39; N 14.70. Found: C 48.14; H 3.17; N 13.51.

EXAMPLE 74

(1R,2R)-3-[2-(2,4-Difluorophenyl)-2-hydroxy-1-methyl-3-(1-H-1,2,4-triazol-1-yl)propyl]-7-iodoquinazolin-4(3H)-one To a cooled (0° C.) solution of the product obtained in example 72 (500 mg, 1.2 mmol) in a mixture of concentrated HCl (3 mL) and ice (4 mL) was added a solution of NaNO$_2$ (88 mg, 1.3 mmol) in H$_2$O (0.5 mL). After 15 min, the resulting mixture was poured to a mixture of KI (1.9 g, 12 mmol) in H$_2$O (10 mL). The reaction mixture was stirred at 25° C. for 15 h. Then, H$_2$O and EtOAc were added, the layers were separated and the organic phase was washed with 1N NaOH and with brine, dried over Na$_2$SO$_4$, filtered, concentrated and purified by flash chromatography to give the title product as a white solid (225 mg, 35%): mp 155°–156° C.; $^1$H NMR (300 MHz, CDCl$_3$) δ (TMS) 8.56 (s, 1H, N═CH—N), 8.18 (d, J=1.5, 1H, arom), 8.02 (d, J=8.5, 1H, arom), 7.85 (dd, J=1.5, J=8.5, 1H, arom), 7.76 (s, 1H, triazole), 7.74 (s, 1H, triazole), 7.48 (dt, J$_d$=6.4, J$_t$=8.8, 1H, arom), 6.9–6.7 (m, 2H, arom), 5.91 (dq, J$_d$=1.5, J$_q$=7.3, 1H, MeCH), 5.53 (d, J=1.5, 1H, OH), 5.14 (d, J=14.2, 1H, CH(H)), 4.00 (d, J=14.2, 1H, CH(H)), 1.29 (d, J=7.3, 3H, CHMe); GC/MS 300 (N-ethylheterocycle, C$_{10}$H$_9$IN$_2$O), 224 (Tr—CH$_2$COHAr, C$_{10}$H$_8$F$_2$N$_3$O); [α]$_D$=−19.3° (c 1, CHCl$_3$). Analysis calculated for C$_{20}$H$_{16}$IF$_2$N$_5$O$_2$: C 45.91; H 3.08; N 13.38. Found: C 45.62; H 3.07; N 13.23.

EXAMPLE 75

(1R,2R)-7-Bromo-3-[2-(2,4-difluorophenyl)-2-hydroxy-1-methyl-3-(1H-1,2,4-triazol-1-yl)propyl]-6-fluoroquinazolin-4(3H)-one Following the procedure described in example 73 but using (1R,2R)-7-amino-3-[2-(2,4-difluorophenyl)-2-hydroxy--methyl-3-(1H-1,2,4-triazol-1-yl)propyl]-6-fluoroquinazolin-4(3H)-one (obtained in example 56) the title compound was obtained as a white solid: mp 185°–186° C.; $^1$H NMR (300 MHz, MeOH-d$_4$) δ (MeOH) 8.52 (s, 1H, N═CH—N), 8.17 (s, 1H, triazole), 8.1–8.0 (m, 2H, arom), 7.64 (s, 1H, triazole), 7.42 (dt, J$_t$=6.5, J$_d$=9, 1H, arom), 7.04 (ddd, J$_d$=2.5, J$_d$=8.5, J$_d$=14, 1H, arom), 6.88 (dt, J$_d$=2.5, J$_t$=8.5, 1H, arom), 6.02 (q, J=7.3, 1H, MeCH), 5.03 (d, J=14.2, 1H, CH(H)), 4.22 (d, J=14.2, 1H, CH(H)), 1.29 (d, J=7.3, 3H, CHMe); GC/MS 270 and 272 (N-ethylheterocycle, C$_{10}$H$_8$BrFN$_2$O), 224 (Tr—CH$_2$COHAr, C$_{10}$H$_8$F$_2$N$_3$O); [α]$_D$=+41° (c 0.1, MeOH).

EXAMPLE 76

(1R,2R)-3-[2-(2,4-Difluorophenyl)-2-hydroxy-1-methyl-3-(1-H-1,2,4-triazol-1-yl)propyl]-6(4-fluorophenyl)thieno[3,2-d]pyrimidin-4(3H)-one Following a similar procedure to that described in example 1 but using 3-amino-5-(4-fluorophenyl)thiophene- 2-carboxylic acid (obtained as described in Hartmann, *Synthesis* 1984, 275) the title compound was obtained as a white solid: mp 118°–127° C.; $^1$H NMR (300 MHz, CDCl$_3$) δ (TMS) 8.60 (s, 1H, N═CH—N), 7.78 (s, 1H, triazole), 7.74 (s, 1H, triazole), 7.70 (m, 2H, arom), 7.50 (dt, J$_d$=6.4, J$_t$=8.8, 1H, arom), 7.49 (s, 1H, thiophene), 7.18 (m, 2H, arom), 6.9–6.7 (m, 2H, arom), 5.98 (dq, J$_d$=1.6, J$_q$=7.3, 1H, MeCH), 5.54 (d, J=1.6, 1H, OH), 5.20 (d, J=14.2, 1H, CH(H)), 4.02 (d, J=14.2, 1H, CH(H)), 1.31 (d, J=7.3, 3H, CHMe); GC/MS 274 (N-ethylheterocycle, C$_{14}$H$_{11}$FN$_2$OS), 224 (Tr—CH$_2$COHAr, C$_{10}$H$_8$F$_2$N$_3$O); [α]$_D$=+12.9° (c 1, CHCl$_3$). Analysis calculated for C$_{24}$H$_{18}$F$_3$N$_5$O$_2$S.1/2H$_2$O: C 56.94; H 3.75; N 13.82; S 6.32. Found: C 57.09; H 3.78; N 13.39; S 6.02.

EXAMPLE 77

(1R,2R)-3-[2-(2,4-Difluorophenyl)-2-hydroxy-1-methyl-3-(1H-1,2,4-triazol-1-yl)propyl]-6(4-nitrophenyl)thieno[3,2-d]pyrimidin-4(3H)-one Following a similar procedure to that described in example 1 but using 3-amino-5-(4-nitrophenyl)thiophene-2-carboxylic acid (obtained as described in Hartmann, *Synthesis* 1984, 275) and recrystallizing the final product from acetonitrile the title compound was obtained as a white solid: mp 272°–273° C.; $^1$H NMR (300 MHz, CDCl$_3$) δ (TMS) 8.63 (s, 1H, N═CH—N), 8.34 (d, J=8.8, 2H, arom), 7.89 (d, J=8.8, 2H, arom), 7.79 (s, 1H, triazole), 7.75 (s, 1H, triazole), 7.69 (s, 1H, thiophene), 7.49 (dt, J$_d$=6.4, J$_t$=8.8, 1H, arom), 6.9–6.7 (m, 2H, arom), 5.98 (dq, J$_d$=1.6, J$_q$=7.3, 1H, MeCH), 5.58 (d, J=1.6, 1H, OH), 5.19 (d, J=14.2, 1H, CH(H)), 4.02 (d, J=14.2, 1H, CH(H)), 1.33 (d, J=7.3, 3H, CHMe); GC/MS 301 (N-ethylheterocycle, C$_{14}$H$_{11}$N$_3$O$_3$S), 224 (Tr—CH$_2$COHAr, C$_{10}$H$_8$F$_2$N$_3$O); [α]$_D$=+17.3° (c 0.23, CHCl$_3$). Analysis calculated for C$_{24}$H$_{18}$F$_2$N$_6$O$_4$S.H$_2$O: C 53.13; H 3.72; N 15.49; S 5.91. Found: C 52.99; H 3.40; N 15.40; S 5.81.

EXAMPLE 78

(1R,2R)-6-(4-Aminophenyl)-3-[2-(2,4-difluorophenyl)-2-hydroxy-1-methyl-3-(1H-1,2,4-triazol-1-yl)propyl]thieno[3,2-d]pyrimidin-4(3H)-one A solution of the above product (388 mg, 0.74 mmol) in EtOH (15 mL) and CHCl$_3$ (15 mL) was treated with 10% Pd/C (88 mg) and H$_2$ at 1 atm under vigorous stirring for 5 h. The catalyst was filtered off through celite, the solvent was removed and the desired product was isolated by flash chromatography (320 mg, 87%): mp 184°–186° C.; $^1$H NMR (300 MHz, CDCl$_3$) δ (TMS) 8.61 (s, 1H, N═CH—N), 7.9–7.7 (m, 6H, arom, triazole), 7.64 (s, 1H, thiophene), 7.49 (dt, J$_d$=6.4, J$_t$=8.8, 1H, arom), 6.9–6.7 (m, 2H, arom), 5.98 (dq, J$_d$=1.6, J$_q$=7.3, 1H, MeCH), 5.55 (d, J=1.6, 1H, OH), 5.20 (d, J=14.2, 1H, CH(H)), 4.3 (br s, 2H, NH$_2$), 4.02 (d, J=14.2, 1H, CH(H)), 1.32 (d, J=7.3, 3H, CHMe); GC/MS 271 (N-ethylheterocycle, C$_{14}$H$_{13}$N$_3$OS), 224 (Tr—CH$_2$COHAr, C$_{10}$H$_8$F$_2$N$_3$O).

EXAMPLE 79

(1R,2R)-3-[2-(2,4-Difluorophenyl)-2-hydroxy-1-methyl-3-(1H-1,2,4-triazol-1-yl)propyl]-6-[4-(methylthio)phenyl]thieno[3,2-d]pyrimidin-4(3H)-one Following a similar procedure to that described in example 1 but using 3-amino-5-[4-(methylthio)phenyl]

thiophene-2-carboxylic acid (obtained as described in Hartmann, *Synthesis* 1984, 275) the title compound was obtained as a white solid: mp 223°–224° C.; $^1$H NMR (300 MHz, CDCl$_3$) δ (TMS) 8.59 (s, 1H, N═CH—N), 7.78 (s, 1H, triazole), 7.74 (s, 1H, triazole), 7.64 (dt, J$_d$=2, J$_t$=8.6, 2H, arom), 7.50 (s, 1H, thiophene), 7.49 (dt, J$_d$=6.4, J$_t$=8.8, 1H, arom), 7.32 (dt, J$_d$=2, J$_t$=8.6, 2H, arom), 6.9–6.7 (m, 2H, arom), 5.98 (dq, J$_d$=1.6, J$_q$=7.3, 1H, MeCH), 5.53 (d, J=1.6, 1H, OH), 5.20 (d, J=14.2, 1H, CH(H)), 4.02 (d, J=14.2, 1H, CH(H)), 2.53 (s, 3H, SMe), 1.31 (d, J=7.3, 3H, CHMe); GC/MS 302 (N-ethylheterocycle, C$_{15}$H$_{14}$N$_2$OS$_2$), 224 (Tr—CH$_2$COHAr, C$_{10}$H$_8$F$_2$N$_3$O); [α]$_D$=+14.3° (c 1, CHCl$_3$). Analysis calculated for C$_{25}$H$_{21}$F$_2$N$_5$O$_2$S$_2$: C 57.13; H 4.03; N 13.33; S 12.18. Found: C 56.99; H 4.12; N 12.96; S 11.80.

EXAMPLE 80

(1R,2R)-3-[2-(2,4-Difluorophenyl)-2-hydroxy-1-methyl-3-(1H-1,2,4-triazol-1-yl)propyl]-6-[4-(methylsulfonyl)phenyl]thieno[3,2-d]pyrimidin-4(3H)-one Following the procedure described in example 51 but using the compound obtained in the preceding example, the title compound was obtained as a white solid: mp 281°–282° C.; $^1$H NMR (300 MHz, CDCl$_3$) δ (TMS) 8.63 (s, 1H, N═CH—N), 8.05 (d, J=8.4, 2H, arom), 7.91 (d, J=8.4, 2H, arom), 7.78 (s, 1H, triazole), 7.74 (s, 1H, triazole), 7.67 (s, 1H, thiophene), 7.49 (dt, J$_d$=6.4, J$_t$=8.8, 1H, arom), 6.9–6.7 (m, 2H, arom), 5.98 (dq, J$_d$=1.6, J$_q$=7.3, 1H, MeCH), 5.57 (d, J=1.6, 1H, OH), 5.19 (d, J=14.2, 1H, CH(H)), 4.02 (d, J=14.2, 1H, CH(H)), 3.10 (s, 3H, SMe), 1.32 (d, J=7.3, 3H, CHMe); GC/MS 334 (N-ethylheterocycle, C$_{15}$H$_{14}$N$_2$O$_3$S$_2$), 224 (Tr—CH$_2$COHAr, C$_{10}$H$_8$F$_2$N$_3$O); [α]$_D$=+13.6° (c 1, CHCl$_3$). Analysis calculated for C$_{25}$H$_{21}$F$_2$N$_5$O$_4$S$_2$: C 53.85; H 3.80; N 12.56; S 11.48. Found: C 53.59; H 3.88; N 12.45; S 11.20.

EXAMPLE 81

(1R,2R)-6-(4-Fluorophenyl)-3-[2-(2-fluorophenyl)-2-hydroxy-1-methyl-3-(1H-1,2,4-triazol-1-yl)propyl]thieno[3,2-d]pyrimidin-4(3H)-one Following a similar procedure to that described in example 76 but using (2R,3R)-3-amino-2-(2-fluorophenyl)-1-(1H-1,2,4-triazol-1-yl)-2-butanol (obtained as described in *J. Org. Chem.*, 1995, 60, 3000–3012) the title compound was obtained as a white solid: mp 213°–225° C.; $^1$H NMR (300 MHz, CDCl$_3$) δ (TMS) 8.63 (s, 1H, N═CH—N), 7.75 (s, 1H, triazole), 7.73 (s, 1H, triazole), 7.71 (m, 2H, arom), 7.49 (s, 1H, thiophene), 7.48 (dt, J$_t$=1.8, J$_d$=8.6, 1H, arom), 7.3–7.2 (m, 1H, arom), 7.17 (tt, J=2, J=8.5, 2H, arom), 7.1–7.0 (m, 2H, arom), 6.04 (dq, J$_d$=1.6, J$_q$=7.3, 1H, MeCH), 5.43 (d, J=1.6, 1H, OH), 5.23 (d, J=14.1, 1H, CH(H)), 4.02 (d, J=14.1, 1H, CH(H), 129 (d, J=7.3, 3H, CHMe); GC/MS 274 (N-ethylheterocycle, C$_{14}$H$_{11}$FN$_2$OS), 206 (Tr—CH$_2$COHAr, C$_{10}$H$_9$FN$_3$O); [α]$_D$=+7.3° (c 1, CHCl$_3$). Analysis calculated for C$_{24}$H$_{19}$F$_2$N$_5$O$_2$S.1/2H$_2$O: C 59.00; H 4.09; N 14.33; S 6.55. Found: C 59,22; H 3,98; N 14.25; S 6.33.

EXAMPLE 82

(1R,2R)-7-Chloro-3-[2-(2-fluorophenyl)-2-hydroxy-1-methyl-3-(1H-1,2,4-triazol-1-yl)propyl]quinazolin-4(3H)-one Following a similar procedure to that described in example 1 but using (2R,3R)-3-amino-2-(2-fluorophenyl)-

1-(1H-1,2,4triazol-1-yl)-2-butanol (obtained as described in *J. Org. Chem.*, 1995, 60, 3000–3012) the title compound was obtained as a white: mp 124°–129° C.; 1H NMR (300 MHz, CDCl$_3$) δ (TMS) 8.65 (s, 1H, N=CH—N), 8.31 (d, J=8.5, 1H, arom), 7.80 (d, J=1.9, 1H, arom), 7.77 (s, 1H, triazole), 7.76 (s, 1H, triazole), 7.6–7.A (m, 2H, arom), 7.3–7.2 (m, 1H, arom), 7.2–7.0 (m, 2H, arom), 6.02 (dq, J$_d$=1.2, J$_q$=7.3, 1H, MeCH), 5.47 (d, J=1.3, 1H, OH), 5.24 (d, J=14.1, 1H, CH(H)), 4.05 (d, J=14.1, 1H, CH(H)), 1.31 (d, J=7.3, 3H, CHMe); GC/MS 207 (N-ethylheterocycle, C$_{10}$H$_9$ClN$_2$O), 206 (Tr—CH$_2$COHAr, C$_{10}$H$_9$FN$_3$O); [α]$^D$= –9.0° (c 0.5, CHCl3). Analysis calculated for C$_{20}$H$_{17}$ClFN$_5$O$_2$: C 58.05; H 4.14; N 16.92. Found: C 58.40; H 4.19; N 16.61.

EXAMPLE 83

In Vitro Activity

In vitro activity was evaluated against *C. albicans, C. krusei*, and *Aspergillus fumigatus* by the agar dilution method. Test strains were either clinical isolates or were obtained from ATCC. Stock solutions containing 800 μg/mL were prepared by solving the test products in 50% ethanol. The culture medium used was Kimmig's agar (K. A., E. Merck) supplemented with 0.5% glycerol. Plates containing serial dilutions (80 to 0.025 gg/imL) of the test products were inoculated with 10 μL of the fungal inocula, containing 10$^5$ colony forming units (cfu)/mL. Plates were incubated at 25° C. during 48 h for *Candida sp.* and during 5 days for *Apergillus fumigatus*. Following incubation MICs (minimal inhibitory concentrations) were determined. Results are shown in the following table:

| IN VITRO ACTIVITIES (MIC in μg/mL) | | | |
|---|---|---|---|
| EXAMPLE No. | C. albicans | C. krusei | Asp. fumigatus |
| 1 | ≦0.03 | 0.63 | 0.31 |
| 2 | ≦0.03 | 1.25 | 1.25 |
| 4 | 0.15 | 0.63 | 10 |
| 5 | 0.07 | 5 | 10 |
| 7 | ≦0.03 | 2.5 | 40 |
| 12 | ≦0.03 | 1.25 | 1.25 |
| 16 | ≦0.03 | 0.63 | 2.5 |
| 17 | ≦0.03 | 0.63 | 20 |
| 20 | 0.31 | 1.25 | 10 |
| 24 | ≦0.03 | 2.5 | 40 |
| 31 | ≦0.03 | 0.07 | 2.5 |
| 38 | ≦0.03 | 5 | 20 |
| 39 | ≦0.03 | 0.15 | 1.25 |
| 50 | ≦0.03 | 0.31 | 2.5 |
| 60 | ≦0.03 | 0.31 | 0.63 |
| 61 | 0.31 | 5 | 5 |
| 67 | 0.31 | 0.63 | 1.25 |
| 68 | 0.31 | 10 | 20 |
| 70 | 0.07 | 10 | 20 |
| 71 | ≦0.03 | 2.50 | 5 |
| 73 | ≦0.03 | 0.31 | 0.31 |
| 74 | ≦0.03 | 0.31 | 0.31 |
| 75 | 0.15 | 1.25 | 2.5 |
| 76 | ≦0.03 | 0.15 | 1.25 |
| 81 | ≦0.03 | 0.31 | 10 |

EXAMPLE 84

In Vivo Activity (Systemic Candidiasis)

Groups of 10 male mice were inoculated i.v. with 0.2 mL of a suspension containing (2–8)×10$^7$ cfu/mL of *Candida albicans*. Compounds were administered orally at 1 mg/kg (or at 10 mg/kg for those compounds marked with an asterisk) at times 1, 4 and 24 h after infection. Following this protocol animals treated with the products of examples 1*, 7, 9, 10, 16, 17, 19, 20, 31, 32, 33, 34, 39, 48, 50, 51, 52, 53, 54, 55, 62, 65, 67, 69, 73*, 74, 75, 76 and 81 showed 100% protection on the day where all the animals in the control group had died (days 24).

EXAMPLE 85

In Vivo Activity (Systemic Aspergillosis)

According to a similar in vivo model of systemic aspergillosis in mice, animals treated with the products of examples 1, 2, 16, 31, 32 and 73 (p.o. 20 mg/kg/day, 5 days) showed 60–100% protection on day 25 postinfection. Mortality in the control group on day 25 was 90%.

As the results of the above tests show, the compounds of the present invention have excellent antifungal properties and therefore are useful for the treatment or prophylaxis of various fungal infections.

We claim:

1. A compound of formula I:

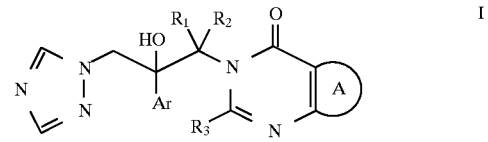

as a racemate, a diastereomer mixture or as a pure enantiomer, wherein:

Ar represents phenyl or phenyl substituted with one or more halogen and/or trifluoromethyl groups;

R$_1$ is C$_1$–C$_4$ alkyl;

R$_2$ is hydrogen or C$_1$–C$_4$ alkyl;

or R$_1$ together with R$_2$ form a C$_2$–C$_4$ polymethylene chain;

R$_3$ represents hydrogen, C$_1$–C$_4$ alkyl, C$_1$–C$_4$ haloalkyl, or cyclopropyl;

A represents a benzene ring or a 5- or 6-membered heterocyclic ring wherein one or more of the ring atoms are selected from the group consisting of N, O and S, which rings can be optionally fused to a benzene ring or to a 5- or 6-membered heterocyclic ring containing one or more heteroatoms selected from N, O and S, and wherein A can be unsubstituted or have 1, 2, 3 or 4 groups W or any of the rings;

the groups W represent C$_1$–C$_4$ alkyl, C$_3$–C$_6$ cycloalkyl, C$_1$–C$_4$ haloalkyl, C$_1$–C$_4$ alkoxy, C$_1$–C$_4$ haloalkoxy, halogen, nitro, cyano, hydroxy, benzyloxy, hydroxymethyl, a group —NR$_4$R$_5$, a group —CONR$_4$R$_5$, a group —CH$_2$—OCO—R$_4$, a group —CO—R$_4$, a group —COO—R$_4$, a group —SO$_z$R$_6$, a group —C(=NR$_4$)NHR$_7$, a group —C(=NR$_7$)OR$_4$, and additionally one of the groups W can also represent 1-pyrrolyl, 1-imidazolyl, 1H-1,2,4-triazol-1-yl, 5-tetrazolyl (optionally substituted with C$_1$–C$_4$ alkyl), 1-pyrrolidinyl, 4-morpholinyl, 4-morpholinyl-N-oxide, a group —X—R$_8$, or a group of formula (i)–(iv):

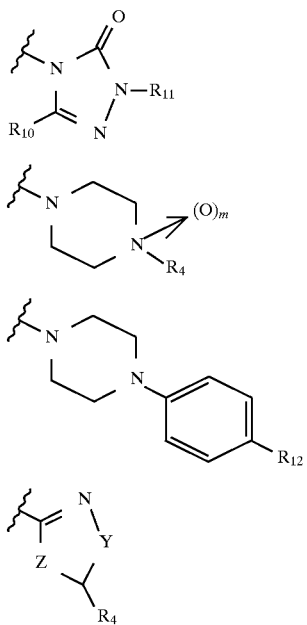

wherein
R₄ represents hydrogen, $C_1$–$C_4$ alkyl, $C_3$–$C_6$ cycloalkyl or aryl$C_{1-4}$ alkyl, wherein aryl represents phenyl or phenyl substituted with one or more $C_1$–$C_4$ alkyl, halogen, $C_1$–$C_4$ haloalkyl, $C_1$–$C_4$ alkoxy or $C_1$–$C_4$ haloalkoxy groups;

R₅ represents hydrogen, $C_1$–$C_4$ alkyl, $C_3$–$C_6$ cycloalkyl, a group —COR₄ or a group —COCF₃;

R₆ represents $C_1$–$C_4$ alkyl;

z represents 0, 1 or 2;

R₇ represents hydrogen, —CONH₂, —COMe, —CN, —SO₂NHR₄, —SO₂R₄, —OR₄, —OCOR₄ or —($C_{1-4}$ alkyl)—NH₂;

X represents a single bond, —O—, —SO$_z$—, —NR₄—, or —C(=O)—;

R₈ represents a phenyl group optionally substituted with one or more groups R₉;

R₉ represents $C_1$–$C_4$ alkyl, $C_3$–$C_6$ cycloalkyl, $C_1$–$C_4$ haloalkyl, $C_1$–$C_4$ alkoxy, $C_1$–$C_4$ haloalkoxy, halogen, nitro, cyano, a group —NR₄R₅, a group —CONR₄R₅, a group —CH₂—OCO—R₄, a group —CO—R₄, a group —COO—R₄, a group —SO$_z$R₆, a group —C(=NR₄)NHR₇, a group —C(=NR₇)OR₄, a group of formula (iv) or R₉ represents a phenyl group (optionally substituted with a group $C_1$–$C_4$ alkyl, $C_1$–$C_4$ haloalkyl, $C_1$–$C_4$ alkoxy, $C_1$–$C_4$ haloalkoxy, halogen, nitro or cyano);

R₁₀ represents hydrogen or methyl;

R₁₁ represents hydrogen, isopropyl, cyclopentyl, cyclopropyl, 2-butyl, 3-pentyl, 3-hydroxy-2-butyl, or 2-hydroxy-3-pentyl;

m represents 0 or 1;

R₁₂ represents halogen, $C_1$–$C_4$ haloalkyl, $C_1$–$C_4$ haloalkoxy, nitro, amino, cyano, or a group of formula (i);

Y represents —CH₂— or —C(=O)—; and

Z represents NH or 0;

and the salts and solvates thereof.

2. A compound as claimed in claim 1 wherein R₁ represents $C_{1-4}$ alkyl and R₂ represents hydrogen.

3. A compound as claimed in claim 2 wherein R₁ represents methyl.

4. A compound as claimed in claim 1 wherein R₃ represents hydrogen, methyl, trifluoromethyl or cyclopropyl.

5. A compound as claimed in claim 1 wherein Ar represents 2-fluorophenyl, 4-fluorophenyl, 2-chloro-4-fluorophenyl, 2,4-dichlorophenyl, 2,4-difluorophenyl, 4-(trifluoromethyl)phenyl or 4-chlorophenyl.

6. A compound as claimed in claim 1 wherein A represents a benzene ring, which can be optionally fused to a benzene ring or to a 5- or 6-membered heterocyclic ring containing one or more heteroatoms selected from N, O and S, or A represents a 5- or 6-membered heterocyclic ring, wherein one or more of said ring atoms are selected from the group consisting of N, O and S, which heterocyclic ring can be optionally fused to a benzene ring, wherein A can be unsubstituted or have 1, 2, 3 or 4 groups W on any of the rings.

7. A compound as claimed in claim 1 wherein A represents a benzene ring or a 5- or 6-membered heterocyclic ring containing one or more heteroatoms selected from N, O and S, wherein A can be unsubstituted or have 1, 2, 3 or 4 groups W.

8. A compound as claimed in claim 1 wherein A represents a benzene ring or a 5-membered heterocyclic ring containing one heteroatom selected from N, O and S or two heteroatoms selected from the pairs N/N, N/O and N/S, wherein A can be unsubstituted or have 1, 2, 3 or 4 groups W.

9. A compound as claimed in claim 8 wherein A represents a benzene, thiophene or thiazole ring, wherein A can be unsubstituted or have 1, 2, 3 or 4 groups W.

10. A compound as claimed in claim 1 wherein A represents a benzene ring, which can be unsubstituted or have 1, 2, 3 or 4 groups W.

11. A compound as claimed in claim 1 wherein A represents a 5- or 6-membered heterocyclic ring containing one or more heteroatoms selected from N, O and S, which can be unsubstituted or have 1, 2, 3 or 4 groups W.

12. A compound as claimed in claim 1 wherein the stereochemistry of the compounds is (1R,2R).

13. A compound as claimed in claim 1 selected from:
(a) (1R,2R)-7-chloro-3-[2-(2,4-difluorophenyl)-2-hydroxy-1-methyl-3-(1H-1,2,4-triazol-1-yl)propyl] quinazolin-4(3H)-one;
(b) (1R,2R)-3-[2-(2,4-difluorophenyl)-2-hydroxy-1-methyl-3-(1H-1,2,4-triazol-1-yl)propyl]-7-trifluoromethylquinazolin-4(3H)-one;
(c) (1R,2R)-3-[2-(2,4-difluorophenyl)-2-hydroxy-1-methyl-3-(1H-1,2,4 -triazol-1-yl)propyl]-7-(2,2,2-trifluoroethoxy) quinazolin-4(3H)-one;
(d) (1R,2R)-6-(4-chlorophenyl)-3-[2-(2,4difluorophenyl)-2-hydroxy-1-methyl-3-(1H-1,2,4triazol-1-yl)propyl] thieno[3,2-d]pyrimidin4(3H)-one;
(e) (1R,2R)-4-[[2-(2,4-difluorophenyl)-2-hydroxy-1-methyl-3-(1H-1,2,4-triazol-1-yl)propyl]-4-oxo-3, 4dihydrothieno[3,2-d]pyrimidin-6-yl]benzonitrile;
(f) (1R,2R)-7-(4-chlorophenoxy)-3-[2-(2, 4difluorophenyl)-2-hydroxy-1-methyl-3-(1H-1,2, 4triazol-1-yl)propyl]quinazolin-4(3H)-one;
(g) (1R,2R)-3-[2-(2,4difluorophenyl)-2-hydroxy-1-methyl-3-( 1H-1,2,4-triazol-1-yl)propyl]-6-[4-[immino (methoxyamino)methyl]phenyl]thieno[3,2-d] pyrimidin4(3H)-one;
(h) (1R,2R)-7-bromo-3-[2-(2,4-difluorophenyl)-2-hydroxy-1-methyl-3-(1H-1,2,4triazol-1-yl)propyl] quinazolin4(3H)-one;

(i) (1R,2R)-3-[2-(2,4-difluorophenyl)-2-hydroxy-1-methyl-3-(1H-1,2,4-triazol-1-yl)propyl]-7-iodoquinazolin-4(3H)-one;

(j) (1R,2R)-3-[2-(2,4-difluorophenyl)-2-hydroxy-1-methyl-3-(1H-1,2,4-triazol-1-yl)propyl]-6(4-fluorophenyl) thieno[3,2-d]pyrimidin-4(3H)-one;

(k) (1R,2R)-3-[2-(2,4difluorophenyl)-2-hydroxy-1-methyl-3-(1H-1,2,4-triazo]-1-yl)propyl]-6-[4-(methylsulfonyl)phenyl]thieno[3,2-d]pyrimidin-4(3H)-one;

(l) (1R,2R)-6-(4-fluorophenyl)-3-[2-(2-fluorophenyl)-2-hydroxy-1-methyl-3-(1H-1,2,4triazol-1-yl)propyl]thieno[3,2-d]pyrimidin-4(3H)-one;

(m) (1R,2R)-7-chloro-3-[2-(2-fluorophenyl)-2-hydroxy-1-methyl-3-(1H-1,2,4-triazol-1-yl)propyl]quinazolin-4(3H)-one;

or a salt or solvate thereof.

14. A process for preparing a compound of formula I as defined in claim 1, which comprises:

(a) reacting a compound of formula II

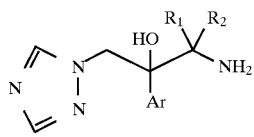

wherein $R_1$, $R_2$ and Ar are as defined in claim 1, first with an acid of formula III

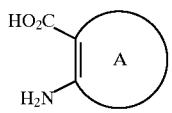

wherein A is as defined in claim 1, in the presence of a condensing agent, and then with an acid $R_3COOH$ (wherein $R_3$ is as defined in claim 1) or a reactive derivative thereof such as the alkyl imidate, amidine, acid chloride, anhydride or orthoester; or (b) reacting a compound of formula II with a compound of formula IV

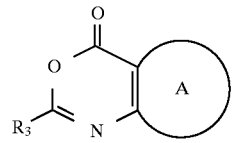

wherein $R_3$ and A are as defined in claim 1; or (c) converting a compound of formula I into another compound of formula I.

15. A pharmaceutical composition which comprises an effective amount of a compound of formula I as claimed in claim 1 or a pharmaceutically acceptable salt or solvate thereof in admixture with one or more pharmaceutically acceptable excipients.

16. A method for the treatment or prevention of a fungal infection in an animal, said method comprising administering a compound of formula I as claimed in claim 1 or a pharmaceutically acceptable salt or solvate thereof to an animal in need of such treatment or prevention.

17. The method of claim 16, wherein said animal is a human.

18. A method for the treatment or prevention of a fungal infection in a plant, said method comprising applying a compound of formula I as claimed in claim 1, or a salt or solvate thereof to a plant in need of such treatment or prevention.

19. The process of claim 14 wherein after steps (a), (b) or (c), said compound of Formula I reacts with an acid to give the corresponding acid addition salt.

* * * * *